(12) United States Patent
Yong et al.

(10) Patent No.: US 7,195,602 B2
(45) Date of Patent: *Mar. 27, 2007

(54) DUAL-CHAMBER LIQUID RECEIVING AND CONTAINING DEVICE

(76) Inventors: Peter A. K. Yong, 3426 Onyx St., Torrance, CA (US) 90503; Mark J. Rispler, 201 Ocean Dr., Manhattan Beach, CA (US) 90266

( * ) Notice: Subject to any disclaimer, the term of this patent is extended or adjusted under 35 U.S.C. 154(b) by 317 days.

This patent is subject to a terminal disclaimer.

(21) Appl. No.: 10/834,405

(22) Filed: Apr. 29, 2004

(65) Prior Publication Data

US 2004/0267159 A1    Dec. 30, 2004

Related U.S. Application Data

(60) Provisional application No. 60/494,773, filed on Aug. 13, 2003, provisional application No. 60/483,782, filed on Jun. 28, 2003.

(51) Int. Cl.
*A61B 5/00* (2006.01)
*B65D 81/00* (2006.01)

(52) U.S. Cl. .................................... 600/573

(58) Field of Classification Search ................ 600/573, 600/575, 576, 579, 580; 604/321, 322, 323, 604/326, 346
See application file for complete search history.

(56) References Cited

U.S. PATENT DOCUMENTS

| | | | |
|---|---|---|---|
| 2,202,123 A | 5/1940 | Strode | |
| 3,499,327 A | 3/1970 | Lane, Jr. | |
| 3,625,064 A | 12/1971 | Hinman, Jr. et al. | |
| 3,635,091 A | 1/1972 | Linzer et al. | |
| 3,680,543 A | 8/1972 | Cox | |
| 3,722,503 A | 3/1973 | Hovick | |
| 3,777,739 A | 12/1973 | Raitto | |
| 3,830,107 A | 8/1974 | Linzer et al. | |
| 3,832,738 A | 9/1974 | Kliemann | |
| 3,878,571 A | 4/1975 | Seeley | |
| 3,881,465 A | 5/1975 | Raitto | |

(Continued)

*Primary Examiner*—Max F. Hindenburg
*Assistant Examiner*—Jeffrey G. Hoekstra
(74) *Attorney, Agent, or Firm*—Walter A. Hackler

(57) ABSTRACT

A dual-chamber device for receiving and containing a liquid, particularly urine, employs a generally cylindrical body having a detachable top cover and an internal, transverse, funnel-shaped wall. The transverse wall has a central circular orifice and divides the body into lower and upper chambers for respectively receiving and retaining fore-stream and mid-stream urine liquid samples. A floatable orifice stopper in the lower chamber is responsive to fore-stream liquid filling the lower chamber to a predetermined level for closing the orifice, so that subsequent, mid-stream urine liquid is received into the upper chamber. An annular float beneath the orifice stopper assures proper stopper closing of the orifice. A bottom cover has an upstanding stopper pushing column and a flexible, spring-like, annular web adjacent the cover periphery. When the urine liquid has been collected in the device and the device is pushed downwardly onto the bottom cover, the web flexes, causing the bottom cover column to force the stopper tightly into the orifice, and locks over center to positively lock the stopper into the orifice to prevent leakage between the two chambers. Other mechanisms, including a urine liquid released compression spring, a urine liquid swellable hydrophilic material, a urine liquid activated effervescent tablet, magnetic elements and urine liquid activated adhesive, are disclosed for positively locking the stopper into the orifice.

3 Claims, 27 Drawing Sheets

U.S. PATENT DOCUMENTS

| | | | |
|---|---|---|---|
| 3,894,845 A | | 7/1975 | McDonald |
| 3,982,898 A | * | 9/1976 | McDonald .................... 422/58 |
| 4,064,760 A | | 12/1977 | Benjamin |
| 4,176,412 A | | 12/1979 | Peterson |
| 4,203,169 A | | 5/1980 | Dale |
| 4,252,132 A | | 2/1981 | Kuntz |
| 4,276,889 A | | 7/1981 | Kuntz et al. |
| 4,301,812 A | | 11/1981 | Layton |
| 4,331,162 A | | 5/1982 | Kuntz et al. |
| 4,494,581 A | * | 1/1985 | Gordon ......................... 141/1 |
| 4,559,049 A | * | 12/1985 | Haan .......................... 604/350 |
| 4,569,090 A | | 2/1986 | Muller |
| 4,573,983 A | * | 3/1986 | Annis ......................... 604/322 |
| 4,769,215 A | * | 9/1988 | Ehrenkranz .................. 422/58 |
| 4,906,566 A | | 3/1990 | Cullimore et al. |
| 5,069,878 A | | 12/1991 | Ehrenkranz |
| 5,105,824 A | * | 4/1992 | Rasch ......................... 600/575 |
| 5,409,473 A | | 4/1995 | Rosenshein |
| 5,518,003 A | | 5/1996 | Allan |
| 5,711,310 A | * | 1/1998 | Vinayagamoorthy et al. .......................... 600/580 |
| 5,744,731 A | | 4/1998 | Dudley |
| 5,766,136 A | | 6/1998 | Cawood |

\* cited by examiner

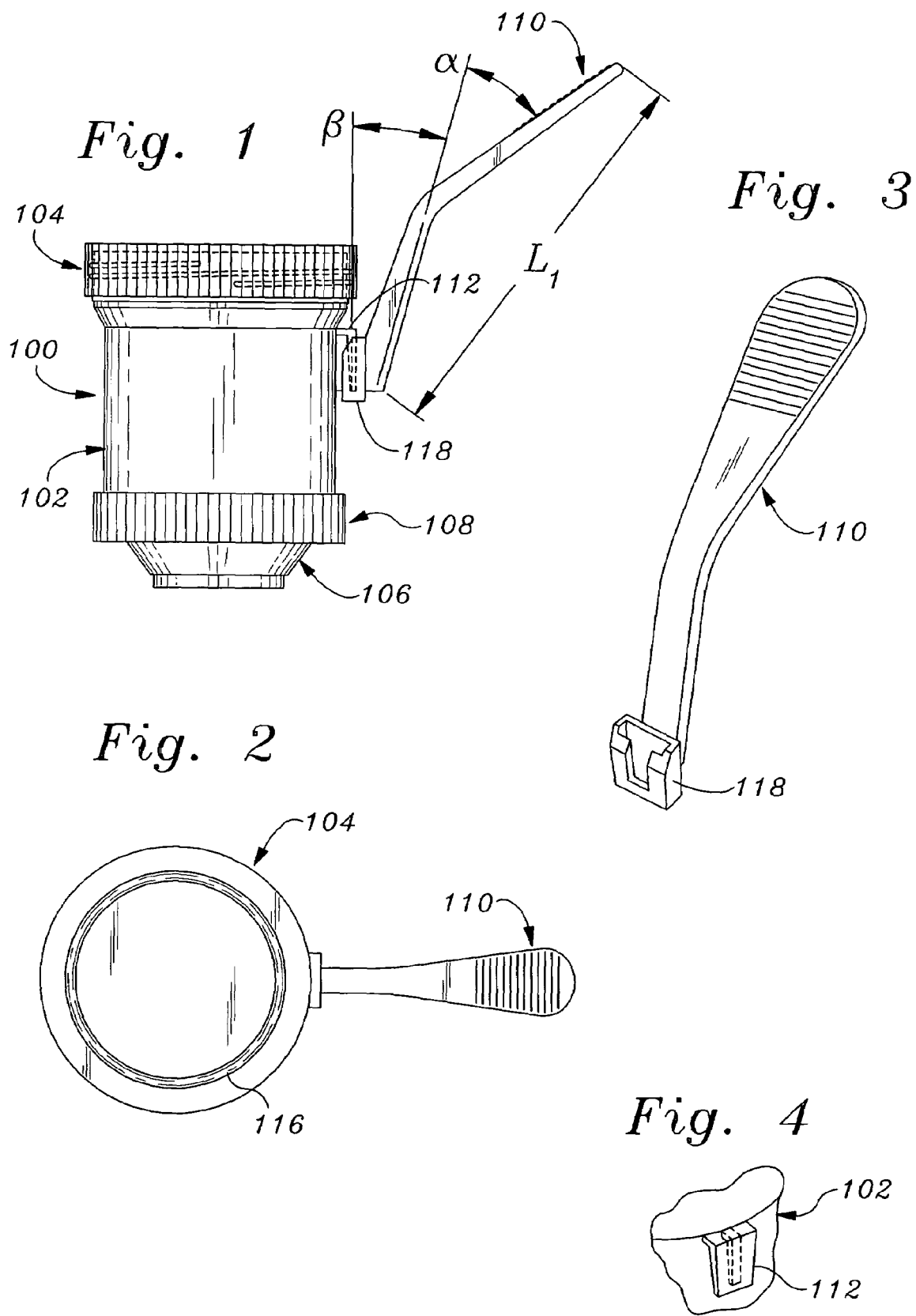

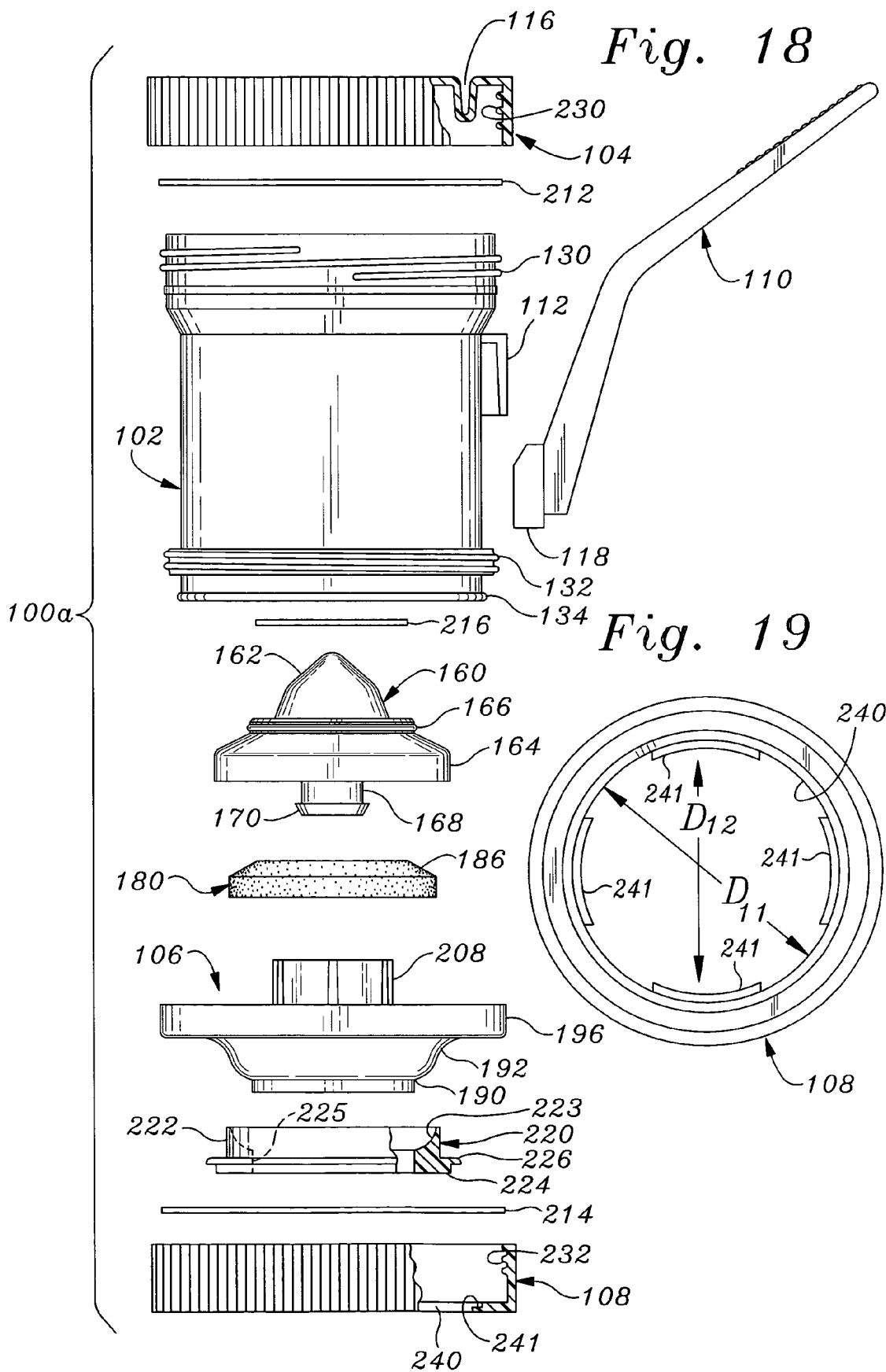

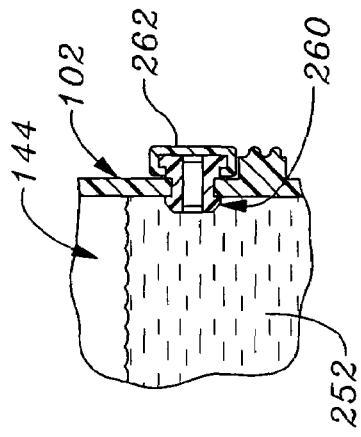
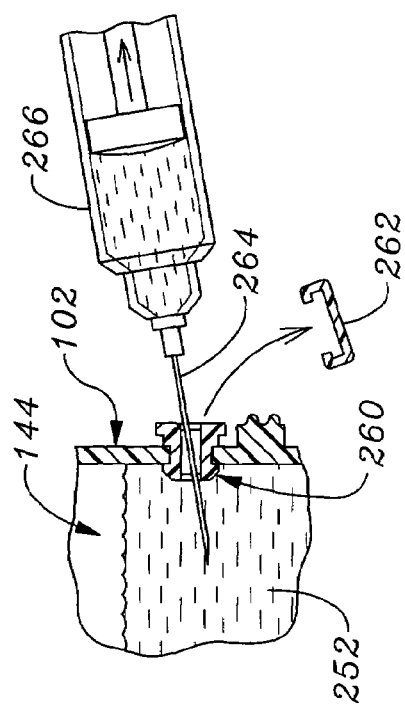
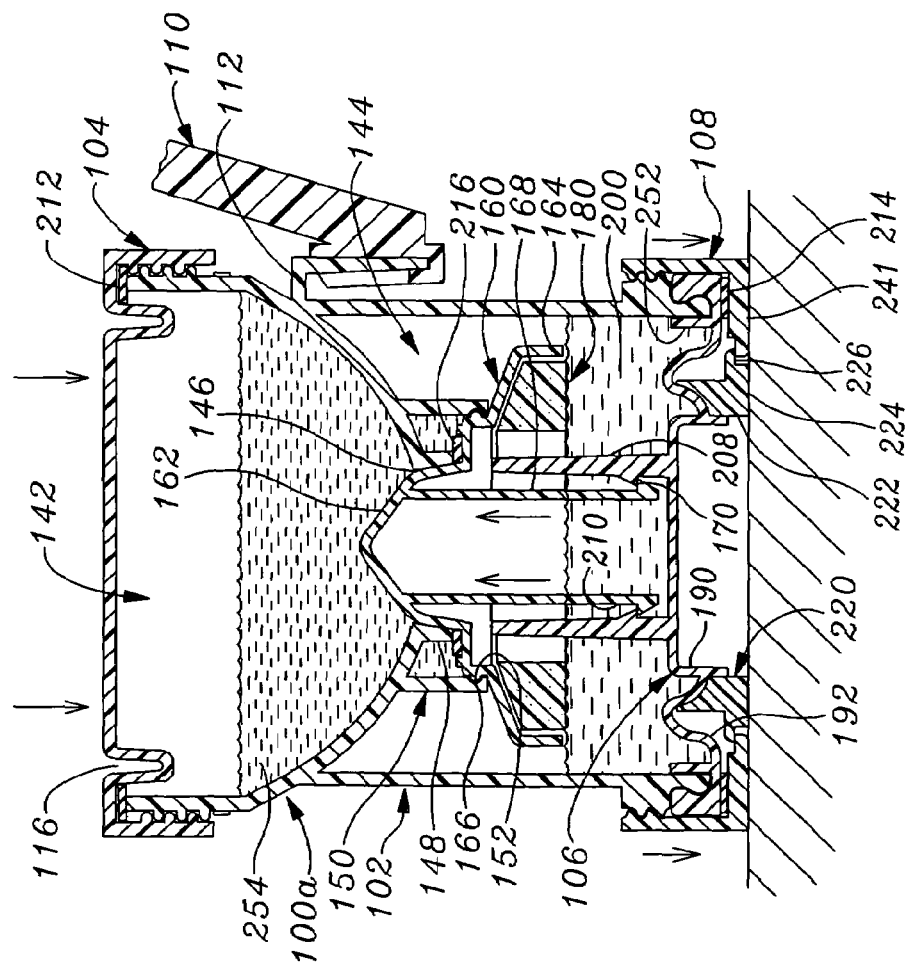
Fig. 25
Fig. 26
Fig. 24

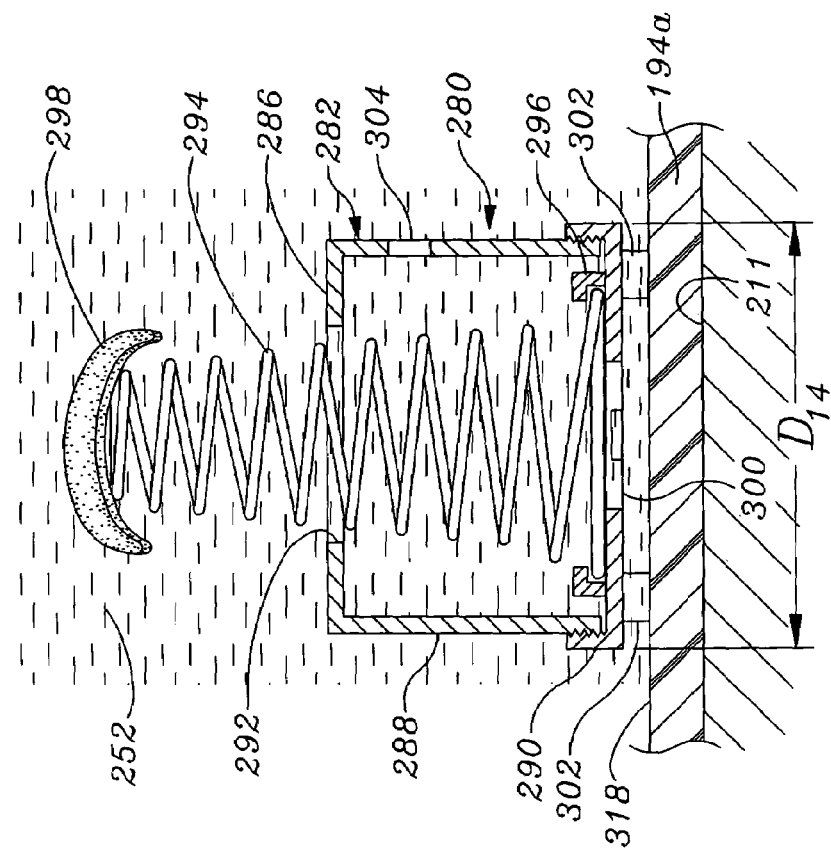
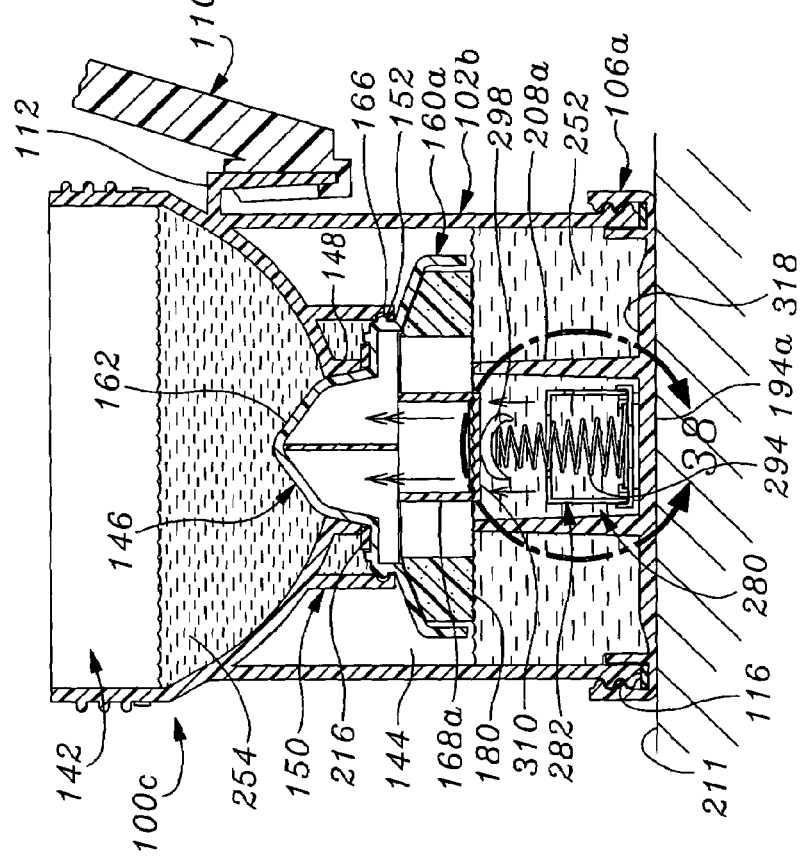

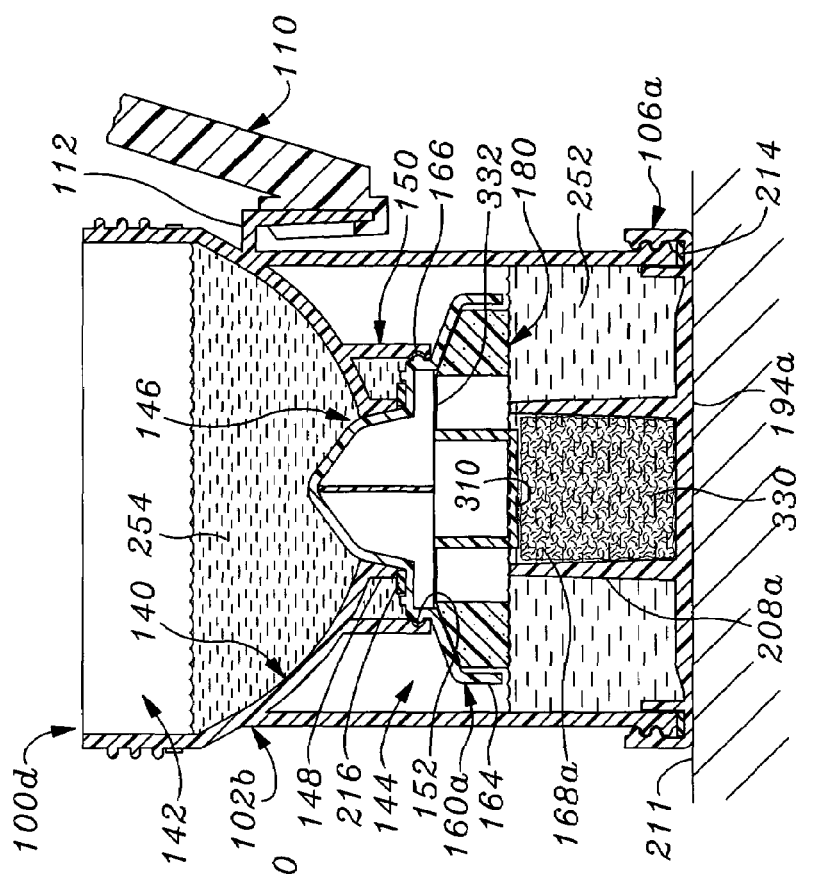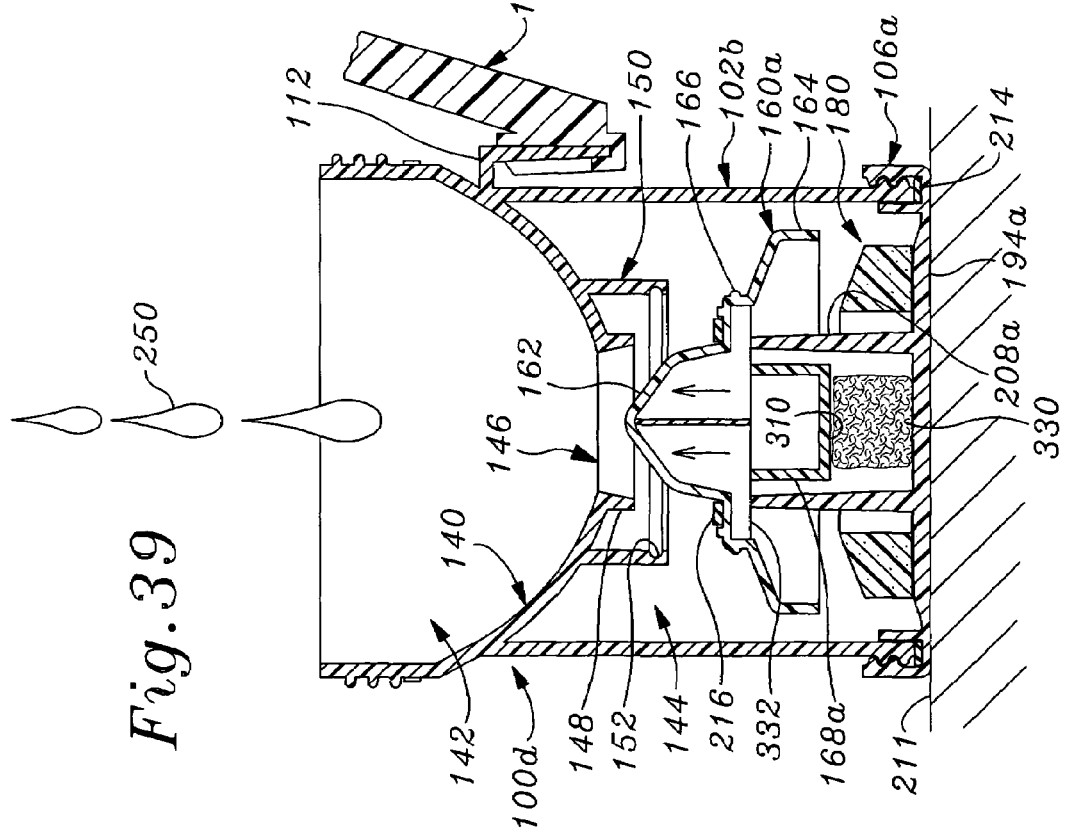

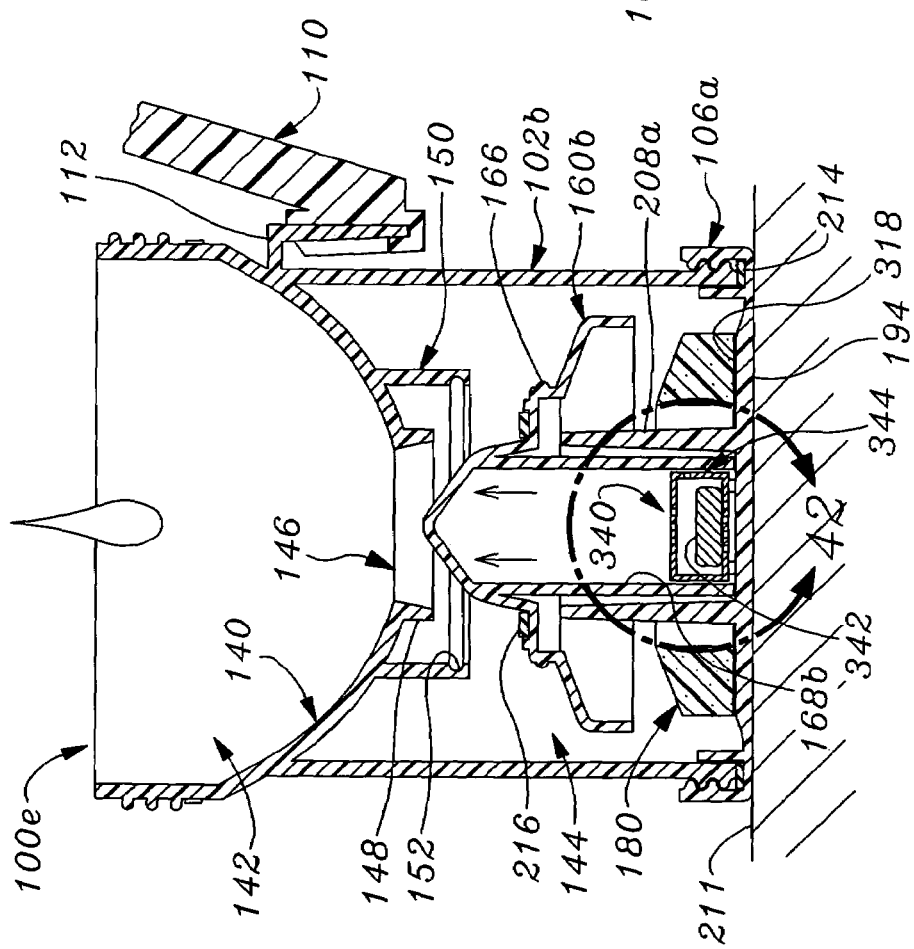

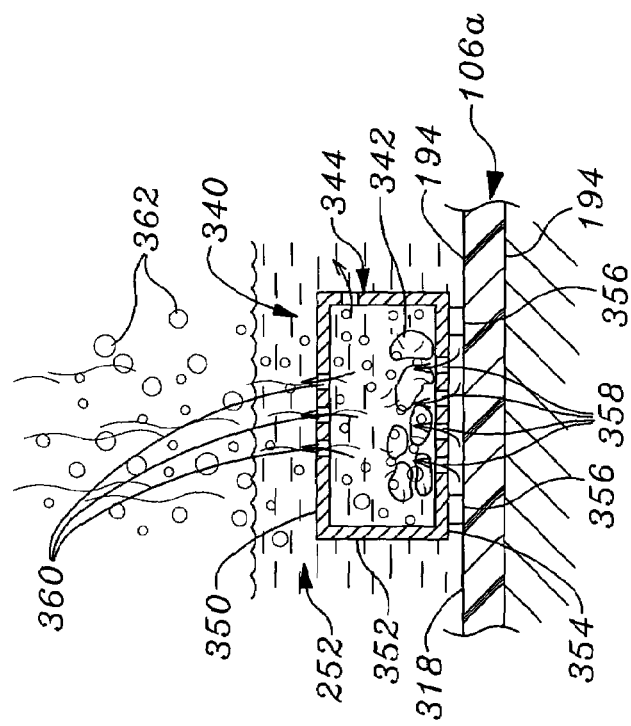
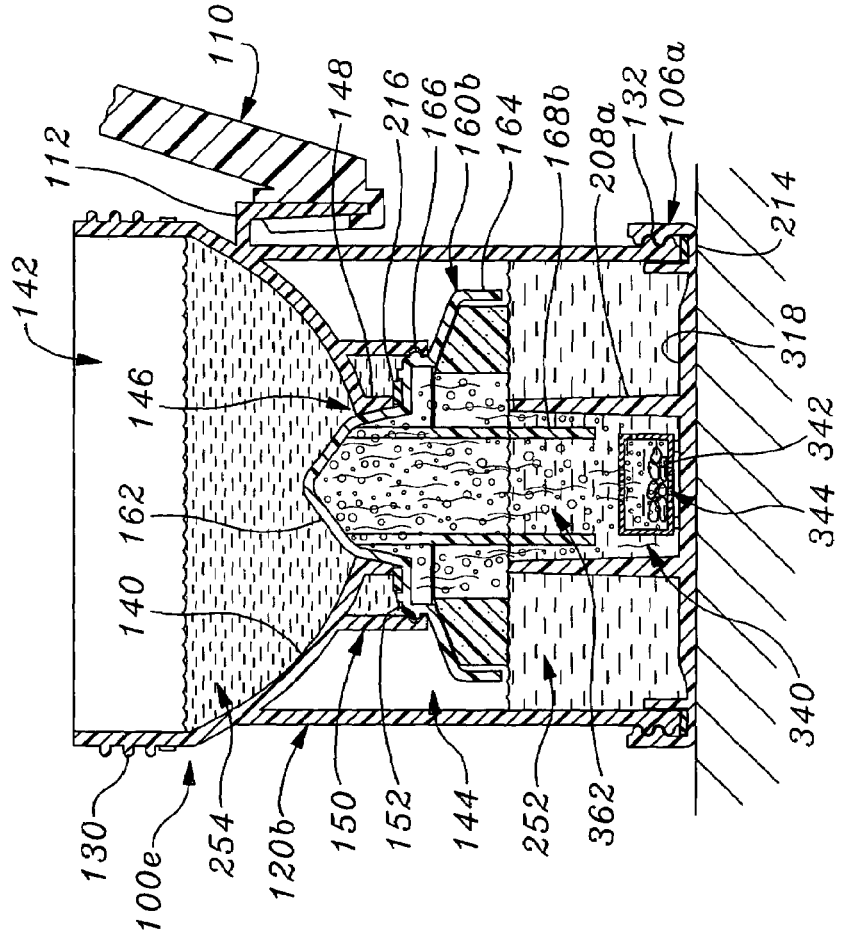
Fig. 43
Fig. 44

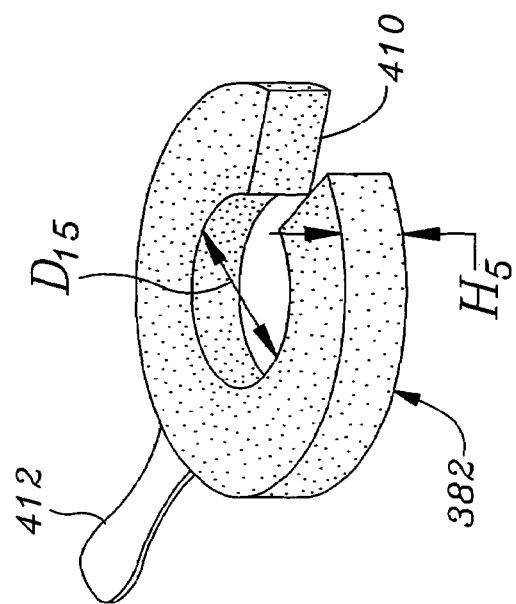
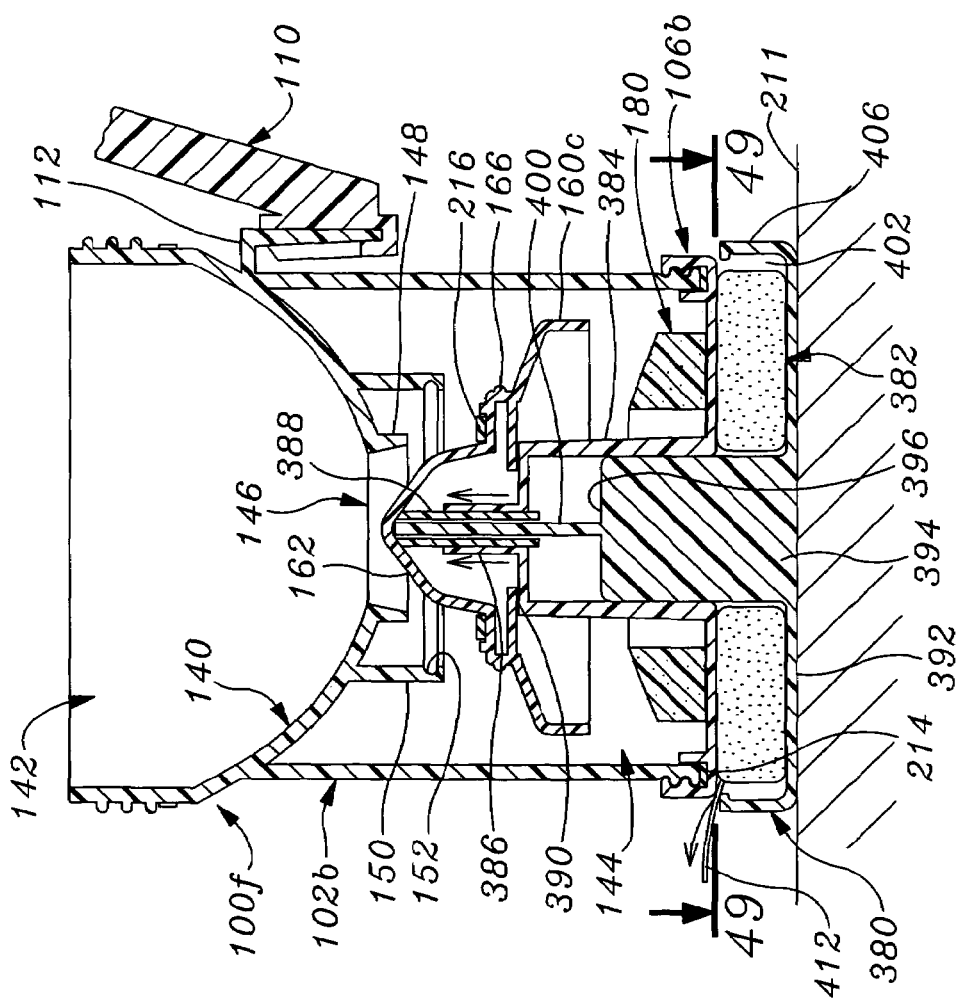

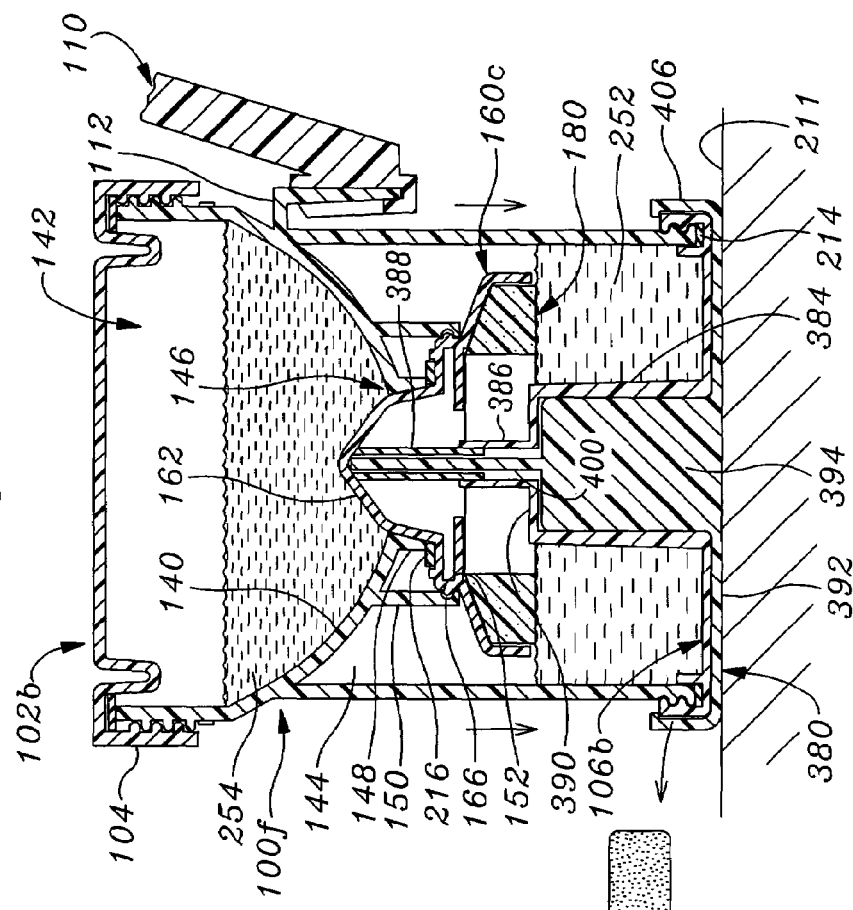
Fig. 47
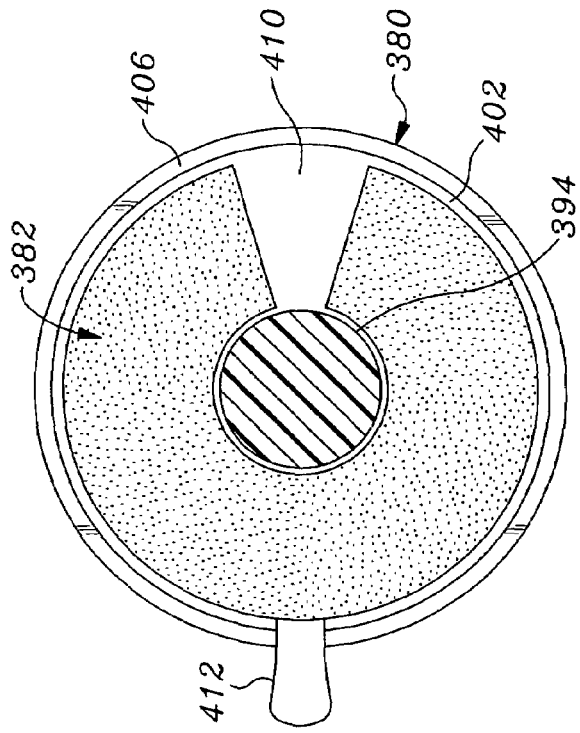
Fig. 48
Fig. 49

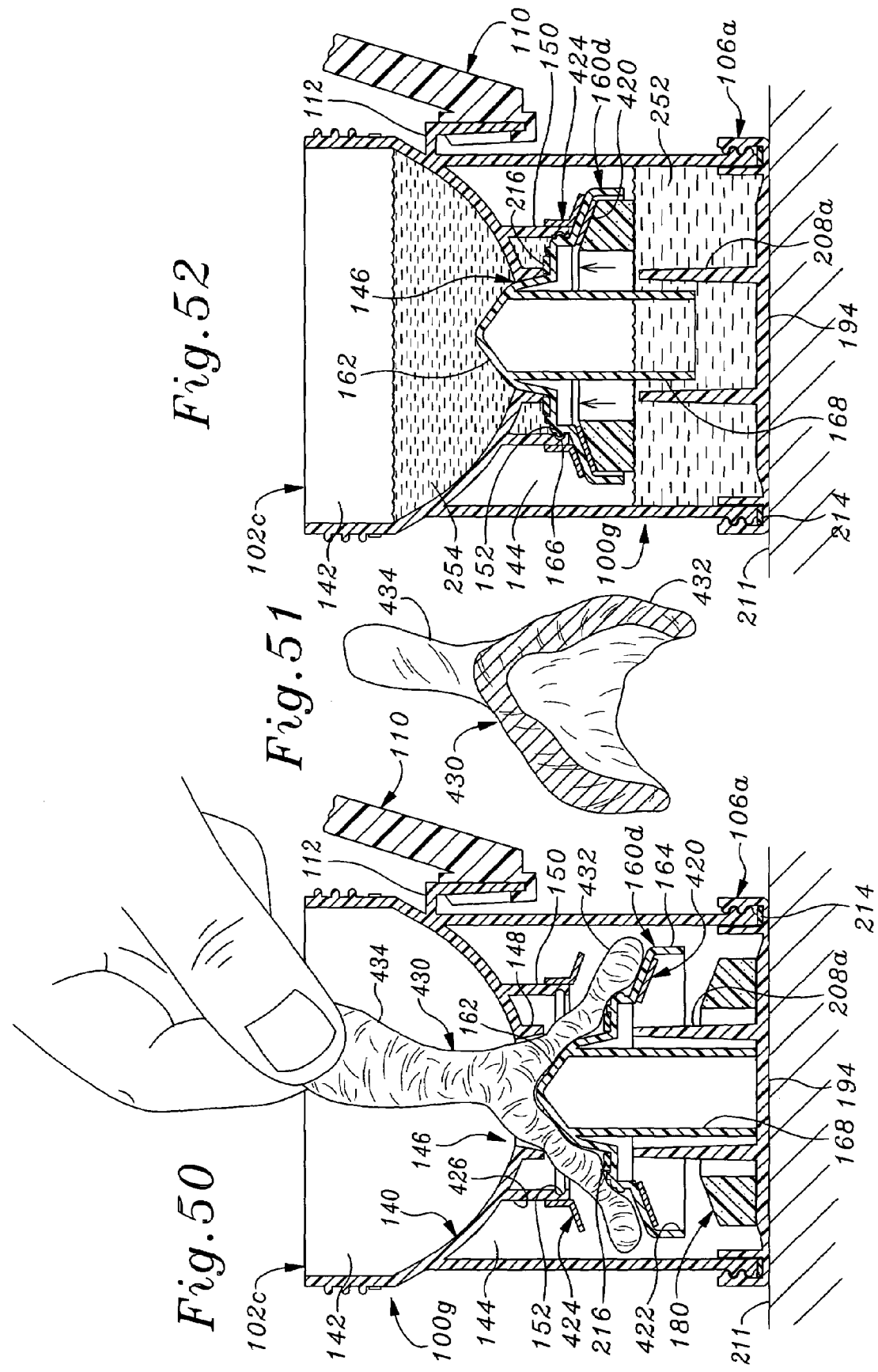

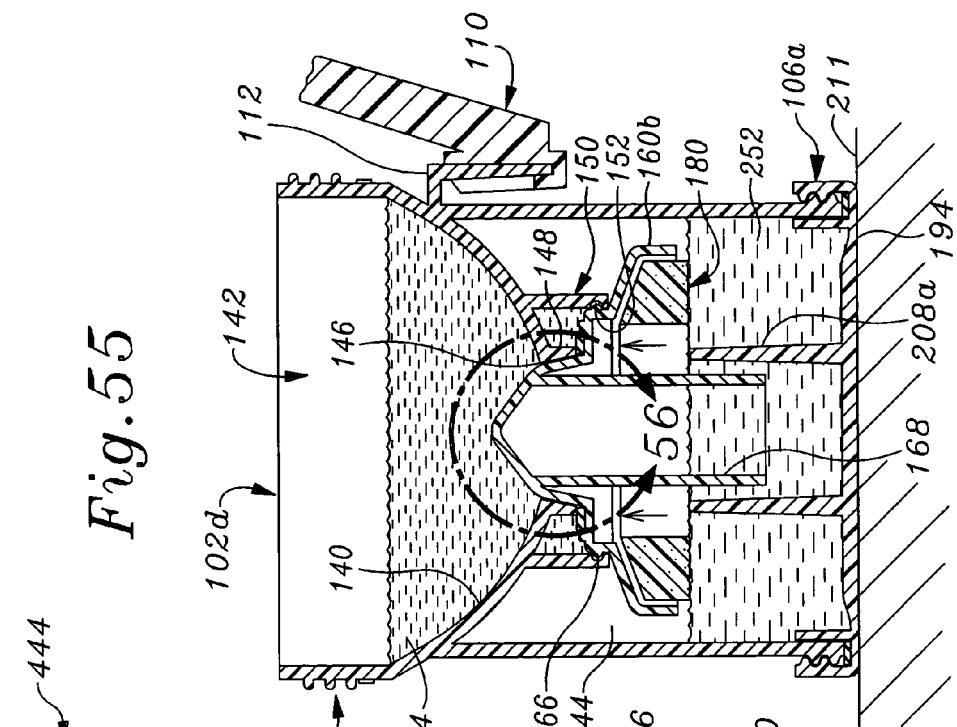
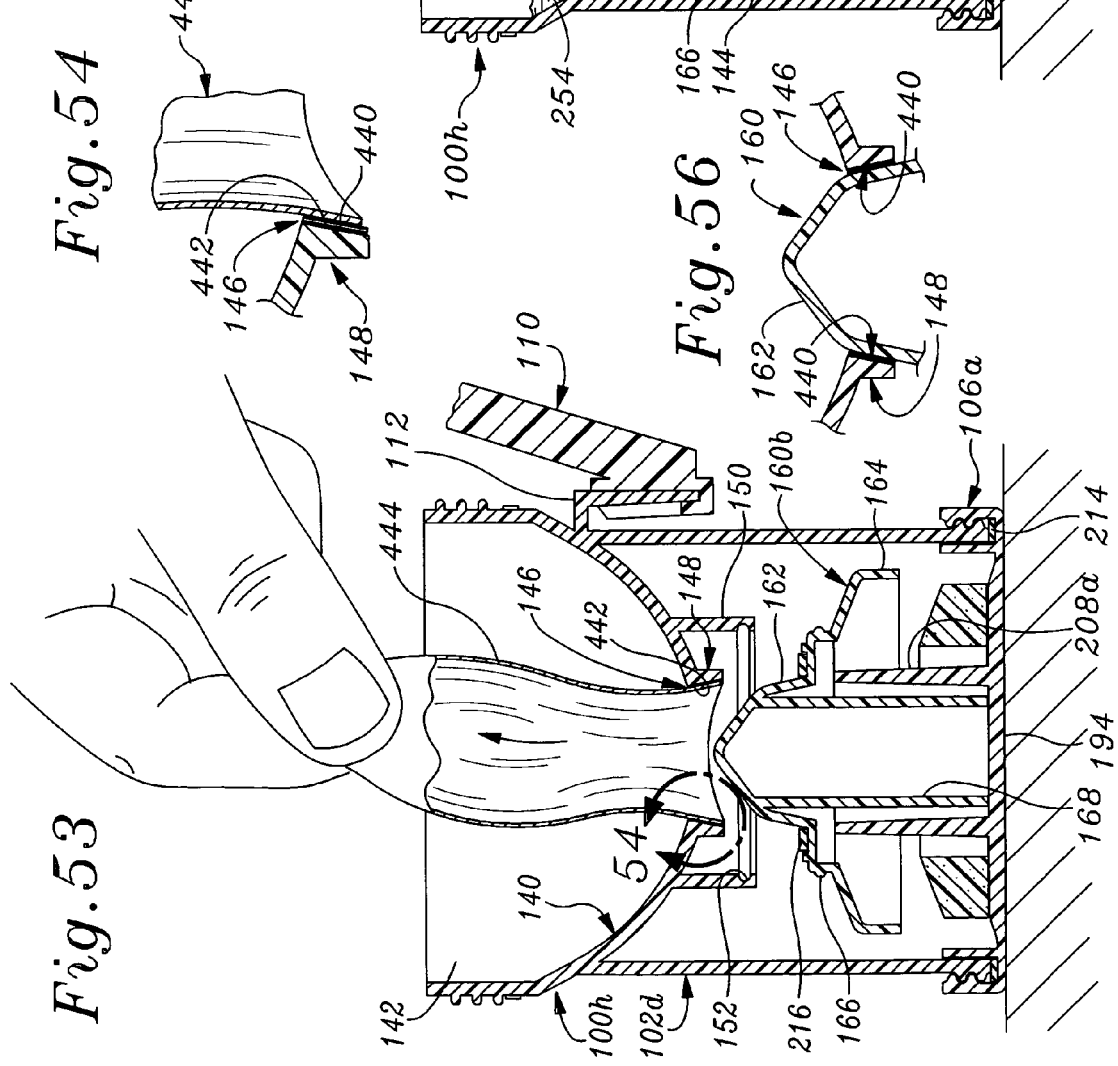
Fig. 53  Fig. 54  Fig. 55  Fig. 56

DUAL-CHAMBER LIQUID RECEIVING AND CONTAINING DEVICE

This application is a utility patent application converted from provisional application Ser. Nos. 60/483,782 and 60/494,773, filed respectively on Jun. 28, 2003 and Aug. 13, 2003.

FIELD OF THE INVENTION

The present invention relates to the general field of devices for collecting and separately containing dual samples of a liquid, more particularly to the collection and separately containing of dual samples of body fluids, and still more particularly to the collection and separate containing of dual samples of urine for analysis.

BACKGROUND OF THE INVENTION

Circumstances often arise wherein a desire or necessity exists for the collection and separate containment of samples of a liquid. As one example, bacterial urinalysis typically requires the collection of a flow of what is generally termed "mid-stream" urine, as described below.

The best mid-stream urine specimen for bacteriologic diagnostic examination is obtained directly from a patient's urinary bladder by catheterization, or by following a very rigorous 10-step body cleaning technique using various antiseptic agents presently available in wide varieties of mid-stream urinary collection systems. Generally, these tedious and highly intimidating cleaning procedures are not strictly followed due to ignorance or non-acceptance, especially by younger female patients.

Added to the facts of inadequacy in the cleaning process and heretofore unavailability of a competent collection system capable of capturing and isolate the mid-stream urinary specimen, a high incidences of "false positive" diagnostic results has always remained a pit-fall in clinical urinary tract infection management.

The initial part of a patient's urinary flow is called fore-stream urine. In females, in particular, this fore-stream urine, while flowing through a poorly cleaned external urogenital tract, is always regarded as contaminated and unsuitable for urinalysis, especially for microbiological or bacteriological examination. More often than not, the fore-stream urine contaminants produce a high incidence of false positive lab test results that are unfortunately derived from external contaminants located around the external urogenital anatomic parts. These apparently "innocent" false contaminants are dragged along the apparently clean urinary stream from the bladder during its excretion process. When this unintentionally contaminated fore-stream urine, while "rinsing" through the patient's urogenital pathway, is collected in a conventional single chamber collection container and then mixes with the later cleaner, mid-stream sample, such badly mixed mid-stream sample is regarded as unsuitable or unacceptable for lab diagnosis procedures.

A problem associated with such mid-stream urine collection is the assuring of an appropriate cleansing fore-stream urine flow (which is not used for the bacteriological analysis). If the fore-stream urine flow is too small, it will result in inadequate rinsing of the urogenital pathway, and the subsequently collected mid-stream urine flow may be contaminated, thereby adversely affecting the bacterial urinalysis. On the other hand, if the fore-stream urine flow is too large, the patient may produce a mid-stream urine flow quantitatively insufficient for urinalysis purposes (typically 6 ml to 12 ml required).

Heretofore, to the knowledge of the present inventors, the most commonly used mid-stream urine collection procedure requires that the patient continuously urinate into a commode (or other receptacle) an amount of about 30 ml to 50 ml of urine (which will be discarded) estimated as sufficient to rinse the anatomical pathway and provide a cleaner specimen for the required uncontaminated mid-stream urine flow, and then finish urinating into a container to collect the subsequent urine flow for analysis. In such a procedure, the amount of discharged fore-stream urine is usually difficult to control for females, and if too small, may result in a contaminated mid-stream urine flow and if too large may result in too small a mid-stream urine flow for accurate biological analysis. Moreover, such a procedure involves the patient uninterrupting her (or his) urine flow to collect the mid-stream flow—something that may be difficult for collecting the mid-stream urine flow. In any event, such a procedure may result in unintended, unsanitary urination onto the patient's hand and/or the urine collection container.

Therefore, it is highly desirable to provide a device which automatically collects, as a first sample, a predetermined amount of fore-stream urine flow and then automatically collects, as a second, separate sample, a mid-stream urine flow. It is further important that the collection device completely isolates the second, clean mid-stream urine sample from the first fore-stream urine sample to prevent contamination of the mid-stream urine sample.

Another example of the need for collecting two contemporary separate urine samples from the same individual is for drug testing of the individual. Particularly when legal issues are or may be involved, two contemporaneous samples of urine from an individual being drug tested are usually desired, if not legally required. A first one of these urine samples is used for on spot drug testing; the second one of the urine samples is (or should be) maintained in a tamper-proof, preserved condition for subsequent drug testing in the event the on spot drug testing results are contested, for example, in a legal dispute, and a second drug test is required.

It is, therefore, a principal objective of the present invention to provide a dual liquid, particularly urine, sample receiving and retaining device, in which the two samples are isolated from one another.

SUMMARY OF THE INVENTION

A dual-chamber liquid receiving and retaining device comprises a liquid receiving and retaining body having a continuous outside wall, an open top and an open bottom; and includes a detachable top cover and a detachable bottom cover for the body. The device body, which is preferably generally cylindrical in shape, is formed having a generally funnel-shaped transverse inner wall that divides the body into upper and lower liquid receiving and retaining chambers, the transverse inner wall tapering downwardly toward an orifice which enables liquid flow communication between the upper and lower chambers. Preferably an annular depending locking flange surrounding the orifice has a narrow inner annular locking recess.

An orifice stopper disposed in the lower chamber, is responsive to liquid filling the lower chamber to a predetermined level that causes the stopper to float upwardly into sealing engagement with the orifice to thereby prevent further liquid flow into the lower chamber. The stopper is preferably formed having a narrow external annular bead shaped to latch into the locking flange annular recess when the stopper is tightly received into the orifice. The orifice is circular in shape and is centrally located in the transverse wall, and the stopper is formed having an upper, conical orifice-sealing region.

It is preferred that the stopper be formed having an outwardly flared circular skirt region. A ring-shaped float having a height selected to provide the predetermined liquid level in the lower chamber is preferably disposed beneath the stopper circular skirt region for providing floating stability to the stopper.

The device body preferably includes a narrow bead around the outside thereof adjacent the open bottom, the bottom cover being configured to snap upwardly over this body bead for attachment of the bottom cover to the body. Also preferably included is a bottom cover locking ring sized to fit over the bottom cover and configured, in conjunction with configuration of the body, for threadable attachment to the body for locking the bottom cover tightly to the body.

A variation device includes an adapter for diverting a strong stream of liquid being received into the device through the open top in a manner which might otherwise prevent the stopper from sealing firmly into the orifice when liquid received into the lower chamber floats the stopper into the orifice. The diverting adapter includes an attachment member removably attached to the open top of the device body in lieu of the top cover. A dome-shaped element attached to attachment member is located directly above the stopper when said member is attached to the device body and when the stopper is floated into the orifice by liquid received into the lower chamber, the dome-shaped element being shaped to divert the strong stream of liquid being received into the device onto a region of the transverse wall surrounding the orifice. The attachment member includes a handle and means for detachably attaching the handle to the attachment member.

Means are preferably included for forcing the stopper into a tight sealing relationship with the orifice so as to assure that liquid does not leak between the upper and lower chambers.

In one case, the stopper forcing means include an annular, spring-like, flexible web formed in the bottom cover around a downwardly extending bottom cover region, web being responsive to a downward pushing on the device onto the downwardly extending bottom cover region for deflecting upwardly in a manner causing a central upstanding region of the bottom cover to engage the stopper and force the stopper upwardly into the orifice and latch the stopper external annular bead into the locking flange annular recess for tightly sealing the orifice against liquid leakage past the stopper. When the web deflects upwardly to cause said bottom cover upstanding region to force the stopper tightly into the orifice and latch the stopper external annular bead into the locking flange annular recess, the web locks over-center to positively lock the stopper into the orifice and latch the stopper external annular bead into the locking flange annular recess so as to assure that liquid does not leak past the stopper between the upper and lower chambers.

There is preferably provided a bottom cover extension which is sized for attachment to the downwardly extending bottom cover region, and sized to provide a larger device body footprint and an additional height to the downwardly extending bottom cover region so as to assure the over-center locking of the web.

A variation dual-chamber device includes a spring disposed in the lower chamber beneath the stopper that is held in a compressed condition by a fiber disc. The disc is responsive to contact by an aqueous liquid received into the lower chamber for a preestablished length of time, which is preferably at least about 20 seconds, that softens the disc sufficiently to release the spring from its compressed condition so as to engage the stopper and force the stopper upwardly into the orifice and latch the stopper external annular bead into the locking flange annular recess for tightly sealing the orifice and to positively lock the stopper into the orifice and latch the stopper external annular bead into the locking flange annular recess so as to assure that liquid does not leak past the stopper between the upper and lower chambers.

Another variation dual-chamber device includes an aqueous liquid, highly expandable, hydrophilic element disposed in the lower chamber beneath the stopper. The hydrophilic element is responsive to contact by an aqueous liquid received into the lower chamber for causing the element to greatly expand into contact with the stopper and force the stopper upwardly into the orifice and latch the stopper external annular bead into the locking flange annular recess for tightly sealing the orifice and to positively lock the stopper into the orifice and the latch the stopper external annular bead into the locking flange annular recess so as to assure that liquid does not leak past the stopper between the upper and lower chambers.

In still another dual-chamber device variation the stopper forcing means includes an aqueous liquid-soluble effervescent tablet disposed in the lower chamber beneath the stopper. The effervescent tablet is responsive to contact by an aqueous liquid received into the lower chamber for providing a large quantity of gaseous bubbles rising to contact the stopper and thereby force the stopper upwardly into the orifice and latch the stopper external annular bead into the locking flange annular recess for tightly sealing the orifice.

An a further variation dual-chamber device, the stopper forcing means includes a secondary bottom cover having a central region extending upwardly through the bottom cover, the central region having an elongate, upstanding stopper engaging pin. A removable spacer is disposed between the bottom cover and the secondary bottom cover to maintain device pre-use separation therebetween. Post-use weight of the device and liquid contained therein causing, when the spacer is removed, causes the secondary bottom cover pin to move upwardly to force the stopper into the orifice and latch the stopper external annular bead into the locking flange annular recess for tightly sealing the orifice. After the spacer is removed and the secondary bottom cover pin forces the stopper tightly into the orifice and latches the stopper external annular bead into the locking flange annular recess, and the device is pressed downwardly onto the secondary bottom cover, the secondary bottom cover is caused to snap upwardly over the bottom cover to cause the secondary bottom cover pin to positively lock the stopper into the orifice and latch the stopper external annular bead into the locking flange annular recess so as to assure that liquid does not leak past the stopper between said upper and lower chambers.

The stopper forcing means of yet another variation dual-chamber device includes a magnetic element fixed to the stopper and another magnetic element fixed to the transverse wall adjacent the orifice, and includes a removable spacer disposed between the stopper and the orifice to prevent device pre-use magnetic attraction of the stopper into the orifice, and wherein as liquid is introduced into the lower chamber to an extent floating the stopper upwardly into the orifice, the stopper is magnetically pulled tightly into the orifice and the stopper external annular bead is latched into the locking flange annular recess by the magnetic elements for tightly sealing the orifice. When the stopper is magnetically pulled tightly into the orifice and the stopper external annular bead is latched into the locking flange annular recess, the magnetic elements positively lock the stopper into the orifice and latch the stopper external annular bead into the locking flange annular recess so as to assure that liquid does not leak past the stopper between the upper and lower chambers.

In a further variation dual-chamber device, an aqueous liquid-activated adhesive is applied to the transverse wall around the orifice and a removable spacer is disposed between the stopper and the orifice to prevent device pre-use adhering of the stopper into the orifice. As liquid is introduced into the lower chamber so as to float the stopper upwardly into the orifice, the adhesive is activated, thereby positively locking the stopper into the orifice so as to assure that liquid does not leak past the stopper between the upper and lower chambers.

In a still further dual-chamber device variation means are provided for diverting a strong stream of liquid being received into the device through the open top thereof so as to prevent the stopper from sealing firmly into the orifice when liquid received into the lower chamber floats the stopper into the orifice. The diverting means includes an attachment member removably attachable to the open top of the device body in lieu of the top cover, and a dome-shaped element attached to the attachment member in a position to be directly above the stopper when the member is attached to the device body and when the stopper is floated into the orifice by liquid received into the lower chamber. The dome-shaped element is shaped to divert the strong stream of liquid being received into the device onto a region of the transverse wall surrounding the orifice. Included is a handle and means for detachably attaching the handle to the attachment member.

It is preferred that the device body be constructed of a rigid plastic material which comprises a high density polypropylene, and that the upper and lower chambers have respective volumes of about 80 ml and about 100 ml for use of the device for urine collection.

In general, there is included an elongate handle and means for detachable attachment of the handle to an upper region of the container outside wall so that the handle projects outwardly therefrom in a generally radial direction, the handle being formed having a gripping region that angles upwardly and outwardly when the handle Is attached to the container outside wall.

In any version of the dual-chamber device there may be included an elastomeric member installed in the container outside wall in the region of the lower chamber, the elastomeric member being puncturable by a hypodermic needle so as to permit the removal of liquid from the lower chamber. The elastomeric element is self-sealing after a hypodermic needle is withdrawn therefrom, and there is preferably included a cover securely covering the elastomeric element, the cover being detachable from the elastomeric element, but not reattachable thereto after removal, thereby providing a visual indication that liquid in the lower chamber may have been tampered with.

BRIEF DESCRIPTION OF THE DRAWINGS

The present invention can be more readily understood by a consideration of the following detailed description when taken in conjunction with the accompanying drawings, in which:

FIG. 1 is an exterior, elevational view of the dual liquid receiving and containing device in accordance with the present invention, showing a device body having a removable top cover, a bottom cover with a locking ring, and an ergonomic handle detachably attached to the device body;

FIG. 2 is a top, plan view of the containment device of FIG. 1 showing features of the top cover and showing the handle detachably attached to the device body;

FIG. 3 is a perspective view of the handle of FIGS. 1 and 2, showing, at a lower end, a T-slot element whereby the handle can be detachably attached to the device body;

FIG. 4 is a detail perspective drawing of a attachment element formed on the collection device body for receiving the T-slot element of the handle of FIG. 3 to thereby enable detachable attachment of the handle to the device;

FIG. 18 is an exploded external elevational drawing of a first variation dual-chamber device, showing the device body, its top cover, the handle, the orifice stopper, the annular float, the bottom cover with the annular web in its un-flexed condition, and the bottom cover locking ring, and showing for the first time a circular bottom cover extension, and further showing top cover, bottom cover locking ring and orifice stopper sealing rings;

FIG. 19 is a top view of the bottom cover locking ring, showing general features thereof;

FIG. 24 is a vertical cross sectional drawing similar to FIG. 23, but showing the upper chamber filled with liquid and the top cover attached to the device body, and showing the device pushed downwardly onto the flat surface sufficiently to flex the bottom cover web in a over-center locking condition pushing the bottom cover base upwardly into the lower chamber and thereby pushing the stopper orifice sealing region into positively locked engagement with the orifice and the orifice locking flange, thereby assuring no liquid leakage can occur between the two chambers;

FIG. 25 is a partial cross sectional view of a variation lower wall region of the device body of FIG. 24, showing the installation in the body outside wall of a capped, hypodermic needle, self-sealing port assembly which may be provided to enable external access to liquid contained in the lower liquid receiving chamber;

FIG. 26 is a partial cross sectional view similar to FIG. 25, showing a hypodermic needle extending through the uncapped, self-sealing port assembly for extracting liquid from the lower liquid containing chamber;

FIG. 35 is a vertical cross sectional drawing, similar to FIG. 22, showing the spring-loaded orifice stopper locking assembly of FIGS. 32–34 in a spring compressed condition installed in the lower chamber of a third variation dual-chamber device in engagement with the orifice stopper, the spring-loaded orifice stopper locking assembly being shown attached to a screw-on flat bottom cover and the orifice stopper being similar to that shown in FIGS. 7–9, except having a shorter depending guide column;

FIG. 36 is a vertical cross sectional drawing similar TO FIG. 24 and corresponding generally to FIG. 36, showing liquid contained in the lower and upper chambers of the third variation device of FIG. 35, showing the orifice stopper floated upwardly into engagement with the orifice between the upper and lower chambers and showing the spring of the spring-loaded orifice stopper locking assembly, still in its compressed state;

FIG. 37 is a vertical cross sectional drawing similar to FIG. 36, but showing the spring of the spring-loaded orifice stopper locking assembly released after the spring retaining element has been degraded by liquid in the lower chamber, the spring thereby forcing the orifice stopper tightly upwardly into the orifice and holding it there against accidental dislodgment;

FIG. 38 is an expanded view of the released spring of the spring-loaded orifice stopper locking assembly of FIG. 37, showing the liquid-degraded spring retaining element pushed upwardly through the housing top opening by the force of the compressed spring, thereby releasing the spring;

FIG. 39 is a vertical cross sectional drawing of a fourth variation dual-chamber device corresponding generally to FIGS. 22 and 35, showing a variation bottom cover containing an expandable, hydrophilic material having an upper surface in contact with the orifice stopper;

FIG. 40 is a vertical cross sectional drawing similar to FIG. 39, showing liquid contained in the upper and lower chambers of the dual-chamber device and showing the expanded hydrophilic material pushing the orifice stopper upwardly into a tight, locked engagement with the orifice;

FIG. 41 is a vertical cross sectional drawing of a fifth dual-chamber device corresponding generally to FIG. 35, showing a bottom cover containing a housing containing a aqueous liquid-activated effervescent tablet;

FIG. 42 is an enlarged side view drawing of the housing containing the liquid-activated effervescent tablet, showing liquid entry apertures and gas escape openings in the housing;

FIG. 43 is a vertical cross sectional drawing similar to FIG. 41, showing the device upper and lower chambers containing a received liquid and showing the orifice stopper floated upwardly into sealing engagement with the orifice and forced tightly thereinto by gases generated by the liquid-activated tablet when contacted by liquid in the lower chamber;

FIG. 44 is an enlarged drawing of the housing containing the liquid-activated effervescent tablet showing generation of gas bubbles when the tablet is contacted by liquid in the device lower chamber;

FIG. 45 is a vertical cross sectional drawing corresponding generally to FIG. 22 and 35 showing a sixth variation dual-chamber device, showing a variation bottom cover and associated variation orifice stopper and showing a secondary bottom cover having an upstanding orifice stopper pushing pin and separated from the primary bottom cover by a removable, highly-flexible split ring spacer;

FIG. 46 is a perspective drawing of the removable, flexible split ring spacer of FIG. 45, showing its general shape and configuration;

FIG. 47 is a vertical cross sectional drawing corresponding generally to FIGS. 24 and 45, showing the lower and upper chambers of the dual-chamber device containing a received liquid and showing the removable, flexible split ring spacer removed so that the weight of the liquid-containing device pushes the secondary bottom cover upwardly into contact with the primary bottom cover, the stopper pushing pin shown pushing the orifice stopper tightly upward into the orifice;

FIG. 48 is a side view of the removable, flexible split ring spacer after its removal from the sixth variation dual-chamber device;

FIG. 49 is a transverse cross sectional drawing taken along line 49—49 of FIG. 45, showing details of the secondary bottom cover with the flexible spacer installed therein;

FIG. 50 is a vertical cross sectional drawing similar to FIGS. 22, 35, 39 and 43 showing a seventh variation dual-chamber device having a flexible spongy or foamy member removably installed between the orifice stopper and orifice to maintain the pre-use separation between annular magnets installed under the flared skirt region of the stopper and adjacent the orifice;

FIG. 51 is a cutaway perspective drawing of the removed spongy or foamy member of FIG. 50, showing general configuration thereof;

FIG. 52 is a vertical cross sectional drawing similar to FIG. 50 showing the flexible spongy or foamy member removed and showing liquid contained in the device upper and lower chambers with the orifice stopper floated upwardly into engagement with the orifice and held in such engagement by the magnets on the stopper and adjacent the orifice;

FIG. 53 is a vertical cross sectional drawing corresponding generally to FIG. 50, showing an eighth variation dual-chamber device having a flexible paper member removably installed between the orifice stopper and orifice to protect an aqueous liquid-activated cement applied around the orifice;

FIG. 54 is an enlarged view showing portions of the flexible paper member covering a region of aqueous liquid-activated cement around the orifice;

FIG. 55 is a vertical cross sectional drawing similar to FIG. 53, showing the flexible paper member removed and with the device upper and lower chambers containing a received liquid and showing the orifice stopper floated upwardly into sealing engagement with the orifice and locked thereinto by the aqueous liquid-activated cement around the orifice;

FIG. 56 is an enlarged view showing the orifice stopper locked into the orifice by the aqueous liquid-activated cement around the orifice;

FIG. 56F depicting installation of the top cover after the liquid has been received into the device body.

In the various FIGS. the same elements and features are given the same reference number and corresponding elements and features are given the original reference numbers followed by an "a," "b," or "c," and so on as appropriate.

DESCRIPTION OF THE PREFERRED EMBODIMENT

Figure 5:
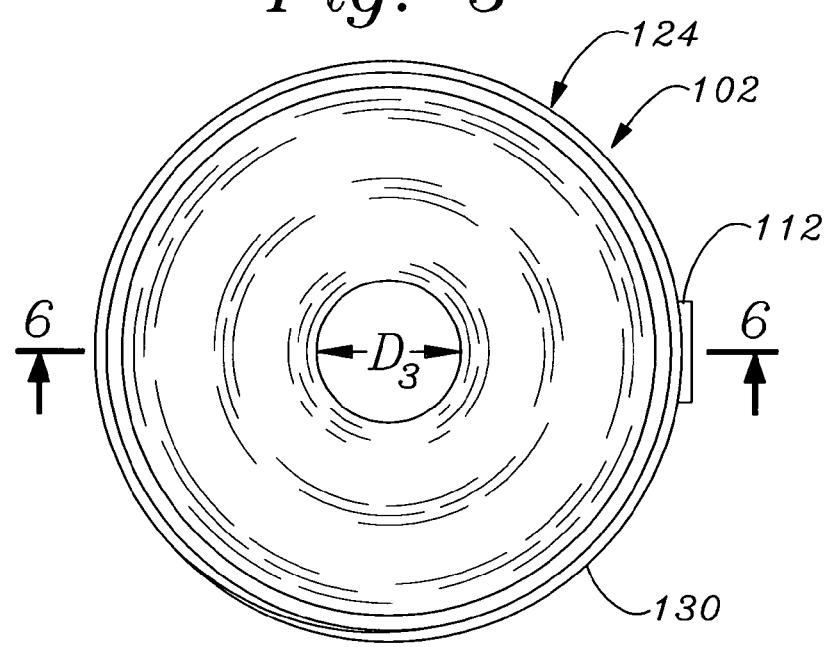
FIG. 5 is a top view of the device body with the top cover removed, showing a transverse wall that divides the body into two chambers, the transverse wall shown having a circular inlet orifice between the two chambers.

There is shown in FIG. 1 a dual-chamber, liquid receiving and containing device 100 (hereinafter, for the sake of brevity, usually referred to as the "dual-chamber device") which may advantageously be used to receive a flow of urine from a patient and contain the urine flow as separate fore-stream and mid-stream flow portions, as described below.

Shown comprising dual-chamber device 100, as more particularly described below, are a generally cylindrical device body or liquid cup 102, a top cover or cap 104 that is detachably attached at an open upper end of the body, a bottom cover or cap 106 that is attached to an open bottom of the body, a bottom cover locking ring 108 that is threaded onto the body to secure the bottom cover to the body (as discussed below), and an angled handle 110 that is detachably attached to the body by a tapered fitting 112 projecting from upper regions of the body.

Top cover 104 is shown in FIG. 2 as having an annular device sealing recess or groove 116. Handle 110 is shown in FIG. 3 as having, at a distal end, an attachment region 118 shaped and sized to fit upwardly onto body fitting 112 (FIG. 4) in a tapered tongue and groove manner. When dual-chamber device 100 (and below-described variations thereof) is used to collect fore-stream and mud-stream urine samples, handle 110 is especially shaped for ergonomically convenient and effective use by female patients for easy accessibility during urine sample collection. As such, handle 110 preferably has an overall length, $L_1$, that may be about 4.5 inches and has a generally central bend, $\alpha$, that may be about 45 degrees; moreover, in combination, handle attachment region 118 and device body fitting 112 mount the handle at an upward angle, $\beta$, of about 30 degrees (FIG. 1).

FIG. 5 shows a top view of device body 102, which may be constructed of a rigid plastic material, such as high density polypropylene, and may be either transparent, translucent or opaque. As shown in the vertical cross section of FIG. 6 device body 102 is formed having an outside wall 124 with a height, $H_1$, which may, for urine specimen collection, be about 3.5 inches; an open top 126 having an outside diameter, $D_1$, that may be about 2.5 inches and an open bottom 128 having an outside diameter, $D_2$, that may be about 2.25 inches. Body wall 124 may have a thickness, $T_1$, that is about 0.05 inches.

A first, externally threaded top cover receiving region 130 is formed on body wall 124 below-adjacent open top 126 and a second, externally threaded bottom lock ring receiving region 132 is formed on the body wall above-adjacent open bottom 128. An external annular bead 134 is formed around body wall 124 at bottom open end 128.

Formed internally across device outer wall 124 is a funnel-shaped transverse inner wall 140 that divides device body 102 into respective upper and lower chambers 142 and 144 having respective volumes for urine collection of about 80 ml and about 100 ml. A central, circular orifice 146 in transverse inner wall 140 is defined by a depending peripheral orifice ring 148 having an entrance opening of diameter, $D_3$, that may be about 0.80 inches, the orifice ring being conically-shaped, that is, is slightly enlarged toward lower chamber 144.

A narrow colored ring 136 on an outside surface 138 of body wall 124 below-adjacent first threaded region 130 is provided as a visual "full" guide when introducing liquid into upper chamber 142.

Depending from transverse inner wall 140 and surrounding orifice ring 148, and extending therebelow, is a stopper securing ring 150 having outer diameter, $D_4$, that may be about 1.25 inches. A narrow, shallow inner annular stopper latching groove or recess 152 is formed around stopper securing ring 148 above-adjacent a stopper securing ring lower edge 156.

Figure 7:
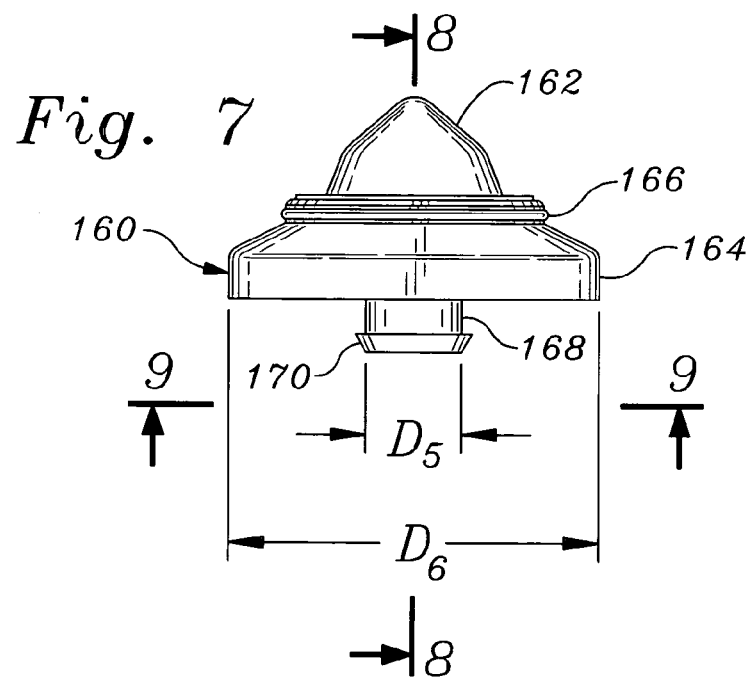
FIG. 7 is a front elevational view of a stopper for closing the orifice in the transverse inner wall, showing an upper, conically-shaped orifice closing region and a lower, flared skirt region having a depending guide column.
Figure 8:
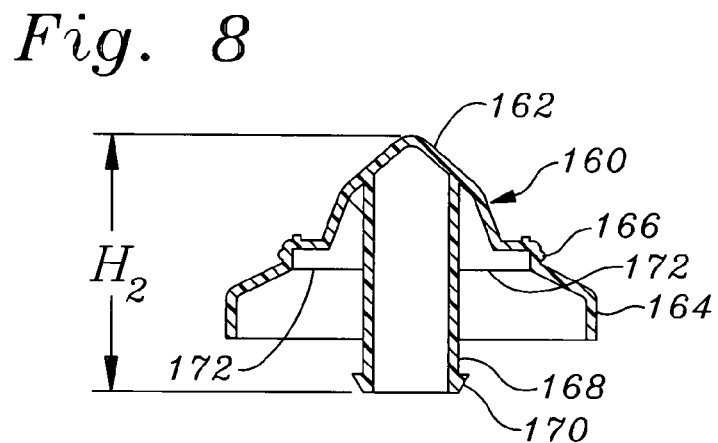
FIG. 8 is a vertical cross sectional drawing taken along line 8—8 of FIG. 7, showing internal structure of the orifice stopper.
Figure 9:
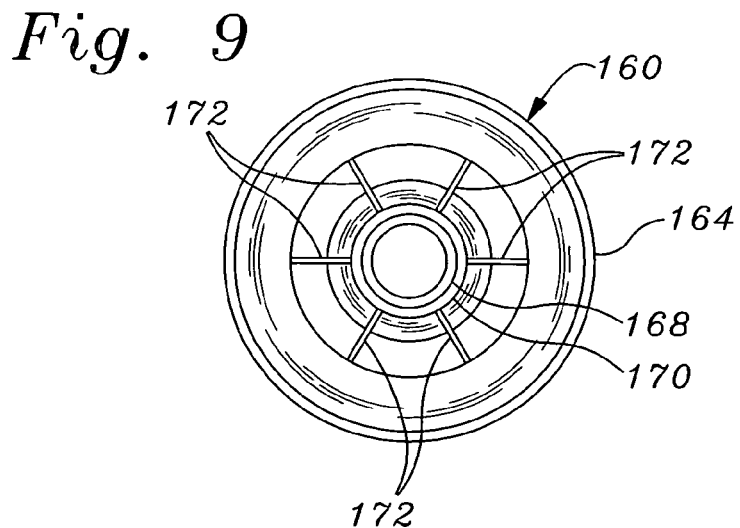
FIG. 9 is a bottom view, looking upwardly along line 9—9 of FIG. 7, showing internal structure of the orifice stopper, in particular ribs for stiffening and strengthening the upper orifice closing region of the stopper.

A buoyant orifice stopper 160, shown in FIGS. 7–9, comprises a hollow, upper, conically-shaped orifice sealing region 162 and a lower, radially-flared skirt region 164, and has an overall height, $H_2$, that may be about 1.25 inches. Orifice sealing region 162 is shaped and sized to fit closely into above-described orifice ring 148 to thereby seal orifice 146. Surrounding a lower region of orifice sealing region 162 is an annular locking bead 166 that is shaped and sized to fit closely into stopper securing ring annular locking groove 152 (also described above). Forming part of orifice stopper 160 is a depending guide or pushing column 168. Formed around a lower region of guide or column 168 is an annular latching ring 170 of saw-tooth shape (FIGS. 7 and 8).

As shown in FIGS. 8 and 9, several (six being shown) internal stiffeners 172 are provided for imparting rigidity to orifice sealing region 162. Stopper 160 is preferably constructed from the same rigid plastic material as device body 102. Orifice stopper skirt 164 preferably has an outside diameter, $D_5$, at a lower skirt peripheral edge 174, which may be about 0.59 inches. Column 168 has an outside diameter, $D_6$, that may be about 1.97 inches.

Figure 6:
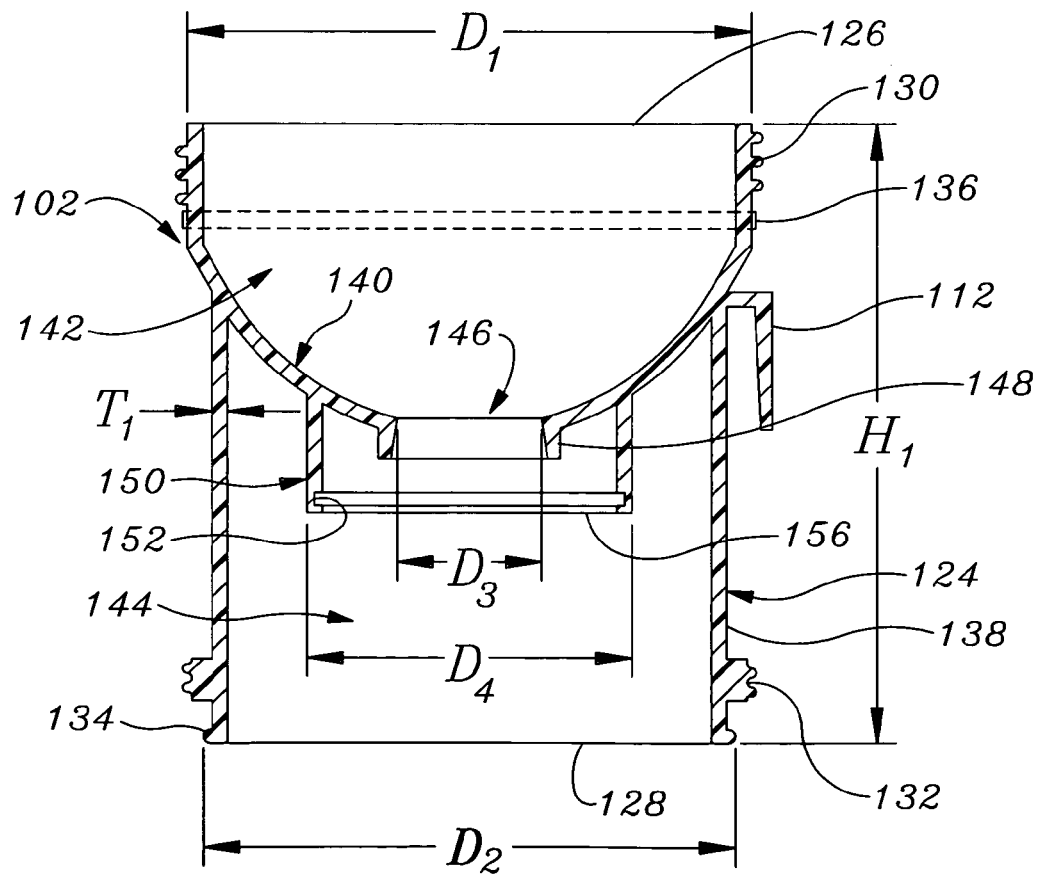
FIG. 6 is a vertical cross sectional view looking along line 6—6 of FIG. 5, showing the transverse inner wall that is generally funnel shaped and which divides the device body into upper and lower liquid receiving and retaining chambers, and showing an annular, undercut locking flange located around the transverse inner wall orifice.
Figure 10:
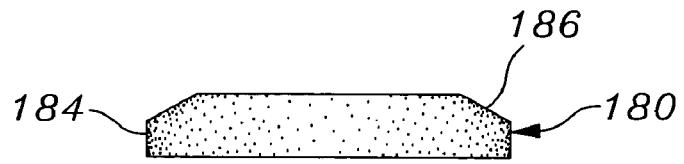
FIG. 10 is a side view of an annular, ultralight float that fits upwardly into the flared skirt region of the orifice stopper shown in cross section in FIG. 8.
Figure 11:
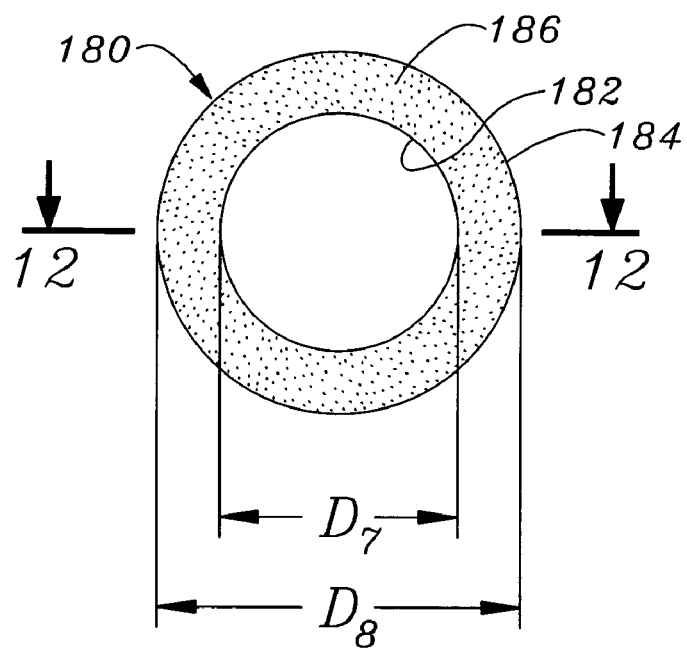
FIG. 11 is a top view of the annular float of FIG. 10, showing a central opening that enables the float to fit loosely around the orifice stopper support and pushing column shown in FIGS. 7–9.
Figure 12:
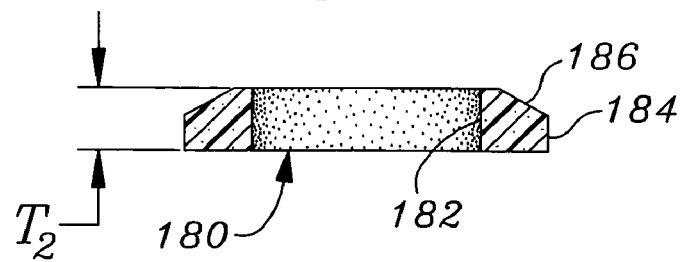
FIG. 12 is a transverse cross sectional drawing taken along line 12—12 of FIG. 11, showing internal configuration of the float.
Figure 13:
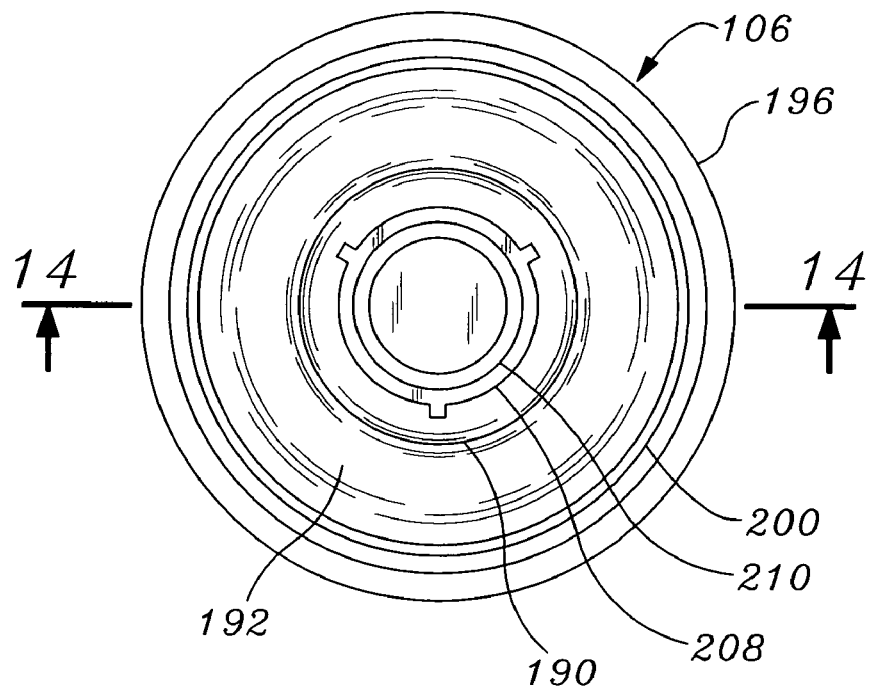
FIG. 13 is a top view of the device body lower cover of FIG. 1, showing construction features.

An annular orifice stopper float 180, shown in FIGS. 10–12, is preferably constructed from a closed cell polystyrene foam so as to be buoyant. Float 180 is shaped and sized to fit upwardly under orifice stopper skirt region 164 to provide buoyancy to orifice stopper 160, as described below. For such purpose, float 180 has an diameter, $D_7$, of an inner surface 182, that may be about 1.0 inch, so as to fit loosely over orifice stopper guide or column 168 and an outside diameter, $D_8$, of an outer surface 184, that may be about 1.57_inches so as to fit loosely under orifice stopper skirt region 164. An upper peripheral region 186 of float 180 is beveled at about 45 degrees so that the float fits under orifice stopper skirt region 164. Float 180 has a thickness, $T_2$, that may, for example, be about 0.39 inch, but is selected according to the desired liquid containing volume of lower chamber 144 (FIG. 6). Float 180 functions to raise orifice stopper 160 into engagement with orifice 146 even when device body 102 is tilted, according to patient skill while discharging urine (or other liquid) into lower chamber 144, even though the orifice stopper is itself generally buoyant.

As shown in FIGS. 13–17, bottom cover 106, which has an overall height, $H_3$, which may be about 1.06 inches, comprises a rigid, upwardly-recessed, central bottom base 190 having a diameter, $D_9$, which may be about 1.18 inches. Central bottom base 190 is surrounded by a thin, flexible, upwardly-arched annular web 192 that has spring-like properties and that extends a distance, $d_1$, that may be about 0.63 inch above a bottom base lower surface 194. Radial outer end of web 192 terminate in an annular, upwardly-extending first devise body attachment flange 196, having an inwardly facing bead 198; and an annular, upwardly-extending second devise body sealing flange 200.

Projecting upwardly from bottom base is an orifice stopper guide 208. Formed around the inside of guide 208 is a saw-toothed latching ring 210 that is shaped in a complimentary manner relative to orifice stopper latching ring 170 (FIGS. 7 and 8). An outside diameter, $D_{10}$, of guide 208 may be about 0.75 inch.

Figure 14:
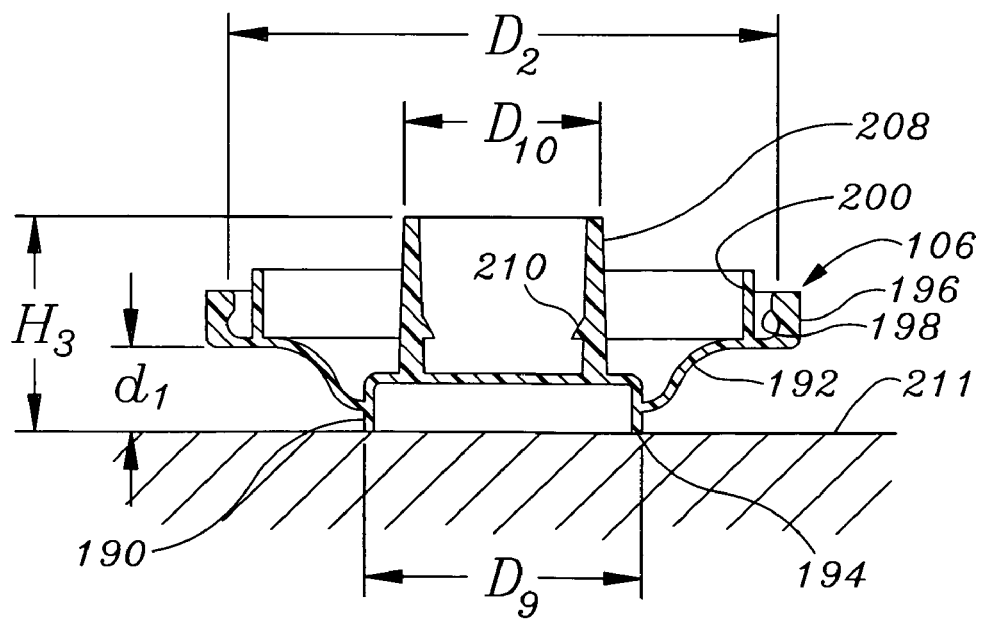
FIG. 14 is a transverse cross sectional drawing taken along line 14—14 of FIG. 13, showing a bottom cover flat base surrounded by a thin, flexible, annular, spring-acting web, the web shown in its normal, un-flexed condition, the bottom cover terminating in a pair of slightly spaced-apart annular upstanding flanges by means of which the bottom cover is attached to the bottom of the device body, and showing a split, upwardly extending pushing column which fits around the orifice stopper guide column of FIGS. 7–9.
Figure 15:
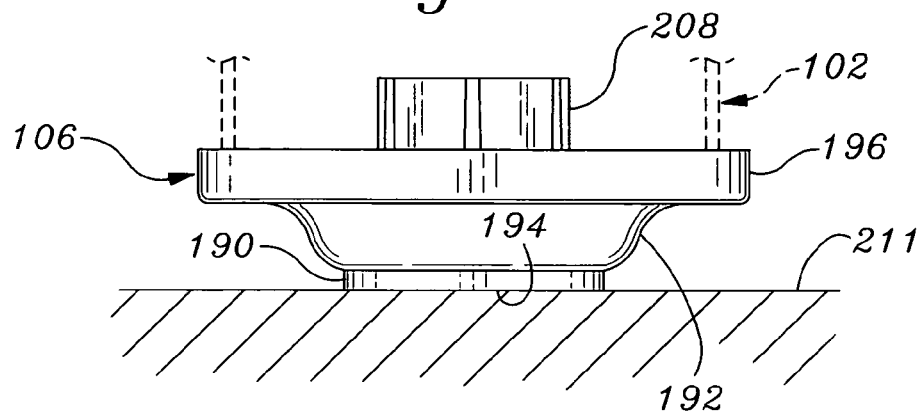
FIG. 15 is a side elevational view of the bottom cover FIGS. 13 and 14, showing the annular web in its un-flexed condition.
Figure 16:
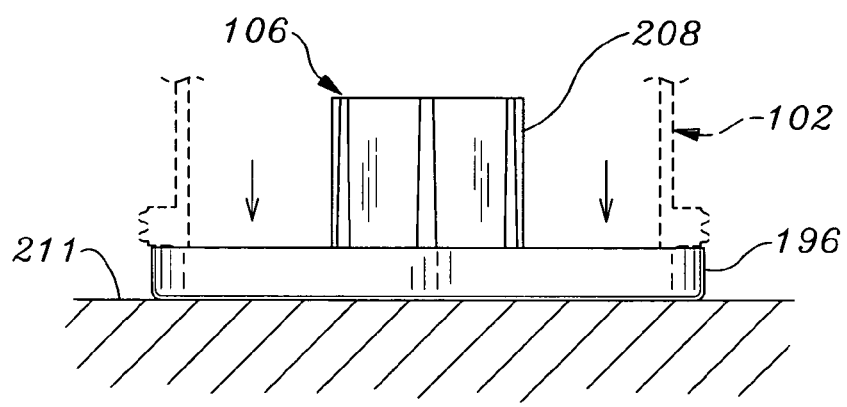
FIG. 16 is a side view of the bottom cover of FIGS. 13–15, showing the annular web in its downwardly-flexed condition associated with pushing the orifice stopper upwardly tightly into the transverse inner wall orifice.
Figure 17:
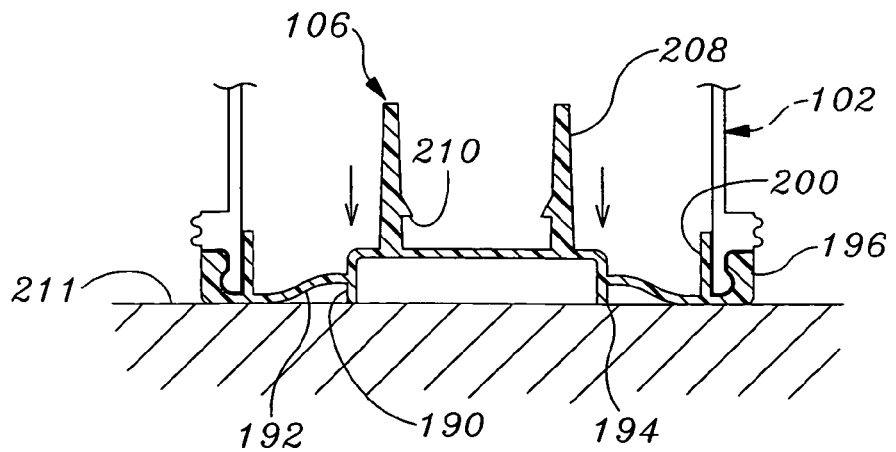
FIG. 17 is a transverse cross sectional drawing similar to FIG. 14, but showing the annular web in its downwardly-flexed condition, thereby forcing the bottom cover pushing column upwardly.

Bottom cover 106 is shown, in a side view, in FIGS. 15–17 attached to device body 102 (shown in phantom lines), FIG. 15 showing bottom cover 106 with annular web 192 in its un-compressed condition. FIG. 16 shows bottom cover 106 with web 192 (not shown) in its compressed condition achieved by pressing downwardly on the bottom cover that is resting on a rigid surface 211 until base region 190 is no longer visible. FIG. 17 is a vertical cross sectional drawing (corresponding to FIG. 14, and derived from FIG. 16) showing bottom cover web 192 flexed into its over-center locking condition as a result of bottom cover 106 being pushed downwardly onto surface 211, thereby pushing orifice stopper 160 upwardly into tight sealing relationship with orifice 146, including "latching" stopper locking bead 166 into orifice locking recess 152, and positively locking the stopper into the orifice to assure no liquid leakage occurs between upper and lower chambers 142 and 144.

Bottom cover 106 is preferably constructed of a relatively high density polypropylene that is less rigid than device body 102 so that web 192 can flex in the manner described above. Because of the relative flexibility of bottom cover 106, the unlikely possibility exists that an offset pushing of the bottom cover (that is, device 100) to flex web 192 into its over-center locking condition, to thereby force stopper 160 tightly into orifice 146 and lock it there (as above-described, some region of bottom cover flange 196 might be dislodged from device body annular bead 134 sufficiently to permit liquid leakage from lower chamber 144. To prevent this remote possibility, bottom cover locking ring 108, which is made of the same rigid plastic material as device body 102, is tightly threaded onto the device body threaded region 132 to lock bottom cover 106 to the device body.

First Variation Dual-Chamber Device 100a:

A first variation dual-chamber device 100a, depicted in disassembled, ordered form in FIG. 18, comprises above described dual-chamber body 102, top cover 104, bottom cover 106, bottom cover locking ring 108, handle 110, orifice stopper 160, orifice stopper float 180, a top cover sealing ring 212, a bottom cover locking ring/ bottom cover sealing ring 214 and a orifice stopper sealing ring 216. Sealing rings 212, 214 and 216 are preferably constructed from rubber (for example, neoprene) or an elastomeric plastic (for example, silicone).

To the above extent previously-discussed dual-chamber device 100 is identical to above-described dual-chamber device 100a, except that included in, and forming the distinguishing feature of, dual-chamber device 100a is a circular bottom cover extension member 220 that fits onto central bottom cover base 190 to provide additional bottom cover height (defined below). Extension member 220 comprises an annular, upwardly-extending attachment flange 222 sized for attaching the member to bottom cover central base 190. An inner surface 223 of flange 222 has a curvature matching the curvature of bottom cover web 192. Flange 222 is preferably colored red for easy visibility. Forming part of member 220 is an enlarged, flat circular support plate region 224 which provides dual-chamber device 100a with a larger "foot print" on surface 211 than that provided by central bottom cover base 190, and which assures over-center locking of bottom cover web 192 and consequent locking of orifice stopper 160 into orifice 146, as described below. Support plate 224 is formed having a relatively thin, narrow annular, peripheral latching region 226 which mates with bottom cover locking ring 108, also as more particularly described below. Support plate region 224 has a central opening 225 that enables extension member 220 to fit upwardly onto bottom cover region 190.

Also shown in FIG. 18, for the first time, is a threaded region 230 on the inside of top cover 104 into which sealing ring 212 is received, and a similar threaded region 232 on the inside of bottom cover locking ring 108 into which sealing ring 214 is received. Top cover threaded region 230 mates with threaded region 130 on device body 102 and bottom cover locking ring threaded region 232 mates with threaded region 132 on the device body. As shown in FIG. 19, bottom cover locking ring 108 has a central aperture 240 with a diameter, $D_{11}$, which may be about 2.09 inches. And a diameter, $D_{12}$, to flaps 241, that may be about 1.97 inches.

Figure 20:
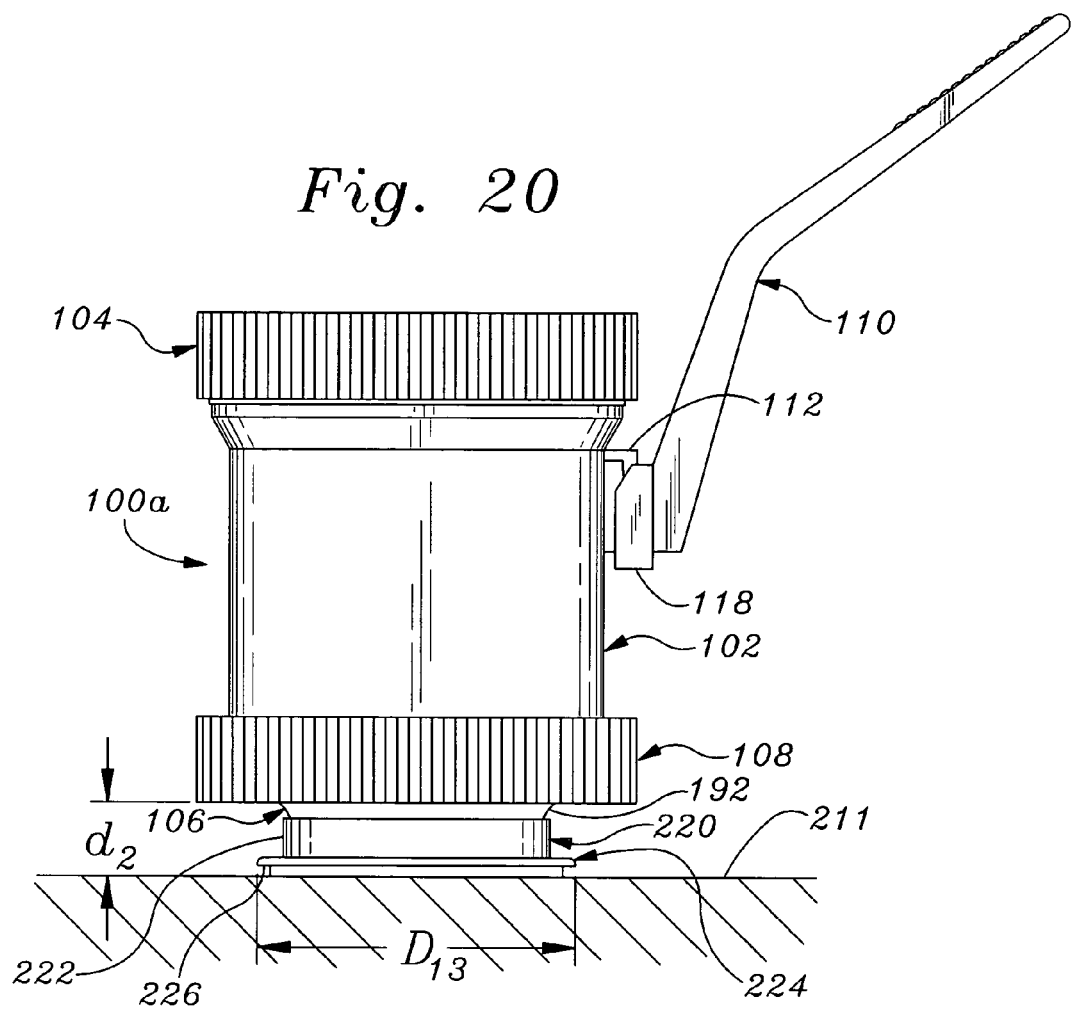
FIG. 20 is an exterior elevational view of a fully assembled, first variation dual sample receiving and containing device in a post-use configuration with the top cover attached to the device body, showing the bottom cover base extension resting on a hard, flat surface.
Figure 21:
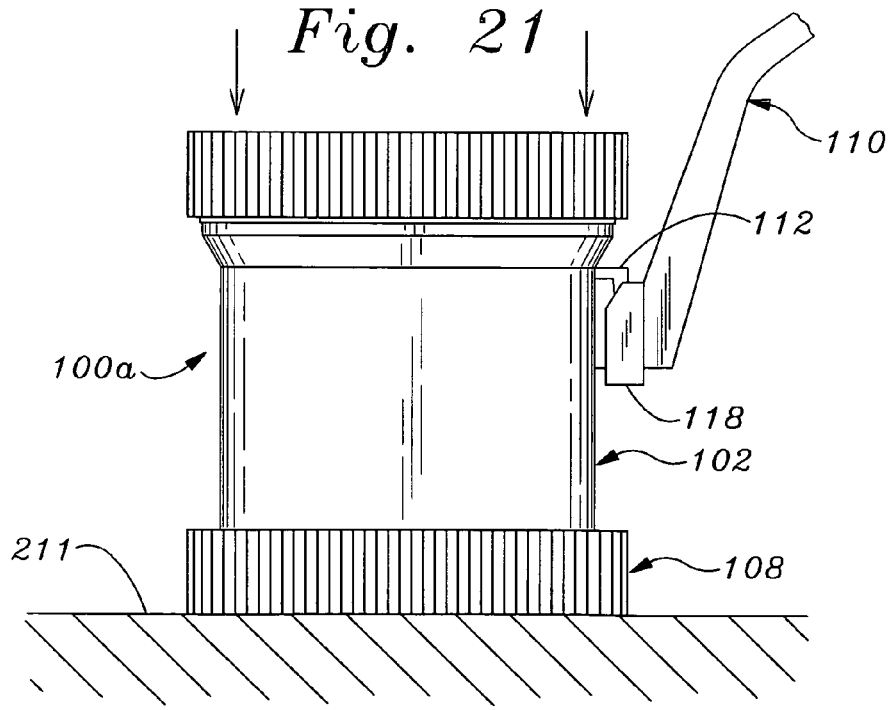
FIG. 21 is an exterior elevational view of the fully assembled first variation dual sample receiving and containing device of FIGS. 18 and 20, the device shown pushed downwardly on a hard, flat surface in a manner forcing the bottom cover base and extension upwardly into the device body for forcing the orifice stopper upwardly into a tight sealing arrangement with the inner wall orifice.

Dual-chamber device 100a is shown in FIG. 20 in its fully assembled, pre-use condition. Bottom cover extension support plate region 224 is shown to have diameter, $D_{13}$. Bottom cover extension 220 provides a distance, $d_2$, from surface 211 to bottom cover locking ring 108, which may be about 0.55 inch, and which is greater than above-described bottom cover height, $d_1$, (FIG. 14). This distance, $d_2$, represents the total amount of flexing of bottom cover web 192 when dual-chamber device 100a is pressed downwardly onto surface 211 as shown in FIG. 21, which depicts the post-use condition of the dual-chamber device. In this regard, the red color of bottom cover extension region 222 is no longer visible when device 100a is in the post-use, compressed condition depicted in FIG. 21.

Figure 22:
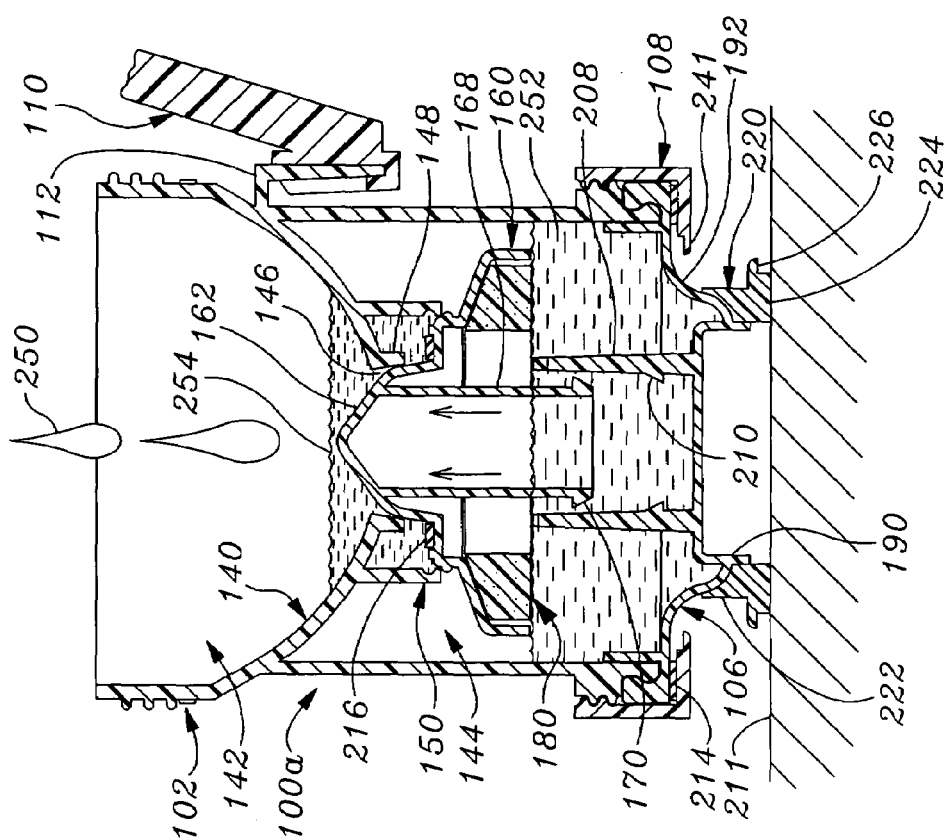
FIG. 22 is a vertical cross sectional drawing of the first variation device of FIGS. 18 and 20–21 in its assembled, pre-use condition, but with the top cover removed, showing the device ready for use, with internal regions of the orifice stopper resting on top of the bottom cover pushing column with the annular float resting on the bottom cover web, and showing the bottom cover locking ring attached to lower regions of the device body, and further showing the bottom base extension attached to the bottom cover base region and supporting the assembled device on a flat surface.

Dual-chamber device 100a is shown, in vertical cross section in FIG. 22, in its fully assembled, pre-use condition with top cover 104 removed, and thus corresponds to FIG. 20 without the top cover. Orifice stopper 160, with orifice stopper seal 216 attached thereto below-adjacent stopper region 162, is shown in its lowermost position, below orifice 146 and resting on bottom cover guide column 210. Float ring 180 is shown in its lowermost position resting on bottom cover web 192. Bottom cover seal 214 is shown installed in bottom cover locking ring 108, threaded region 232 of which is shown treaded onto device body threaded region 132.

Figure 23:
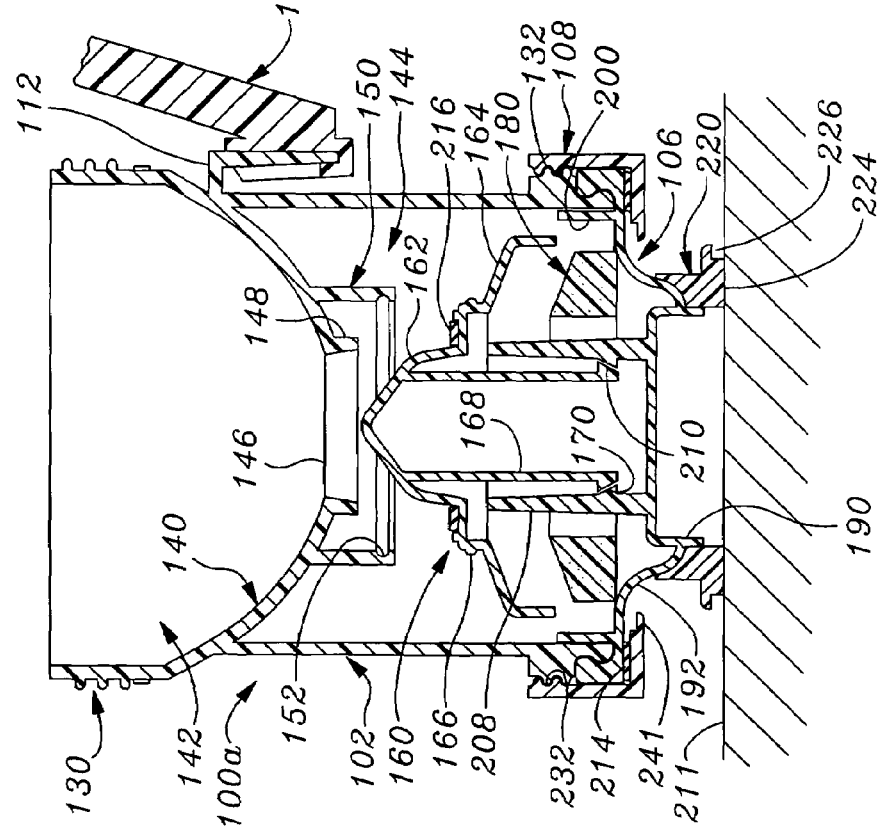
FIG. 23 is a vertical cross sectional drawing similar to FIG. 22, but showing a flow of liquid being discharged into the upper chamber of the first variation device, with the lower chamber having first been filled to a level causing the annular float to push the stopper upwardly until the upper orifice sealing region of the stopper engages the orifice between the upper and lower chambers so as to stop the flow of liquid into the lower chamber and prevent liquid leakage between the two chambers.
Figure 27:
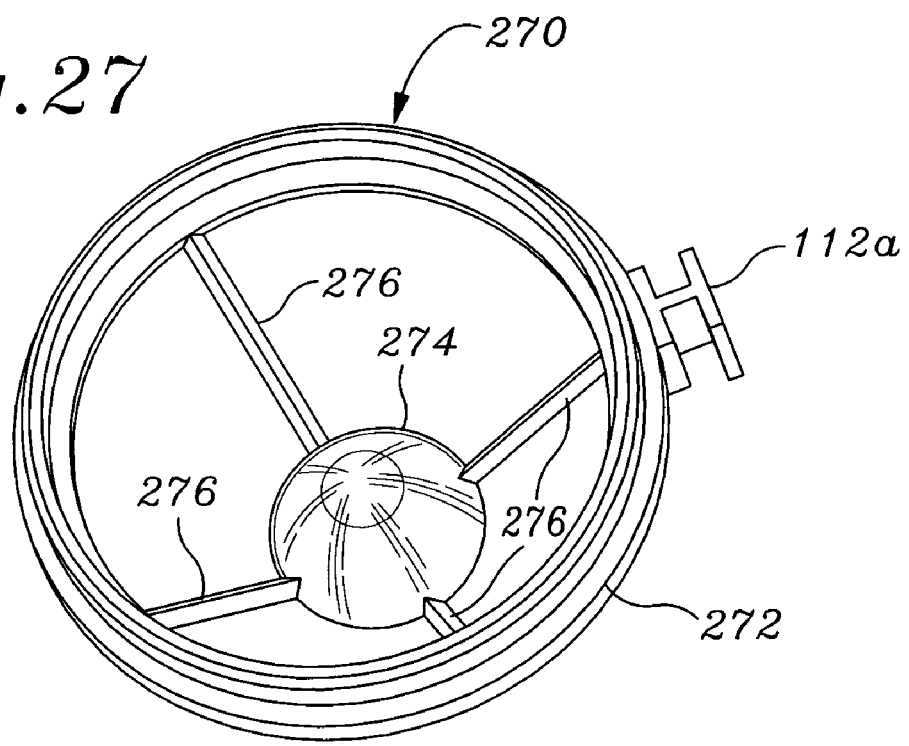
FIG. 27 is a top perspective of an optional flow diverter and sanitary barrier member configured for attachment to the open top of a dual-chamber device similar to that depicted in FIGS. 18–24, showing a central dome-shaped liquid diverter supported by four ribs, the liquid diverter preventing a strong flow of liquid entering the device upper chamber from impinging directly onto the orifice stopper and possibly unseating it when the stopper reaches its intended orifice sealing engagement, also showing a fitting whereby the device handle can be detachably attached to the flow diverter and sanitary barrier member.
Figure 28:
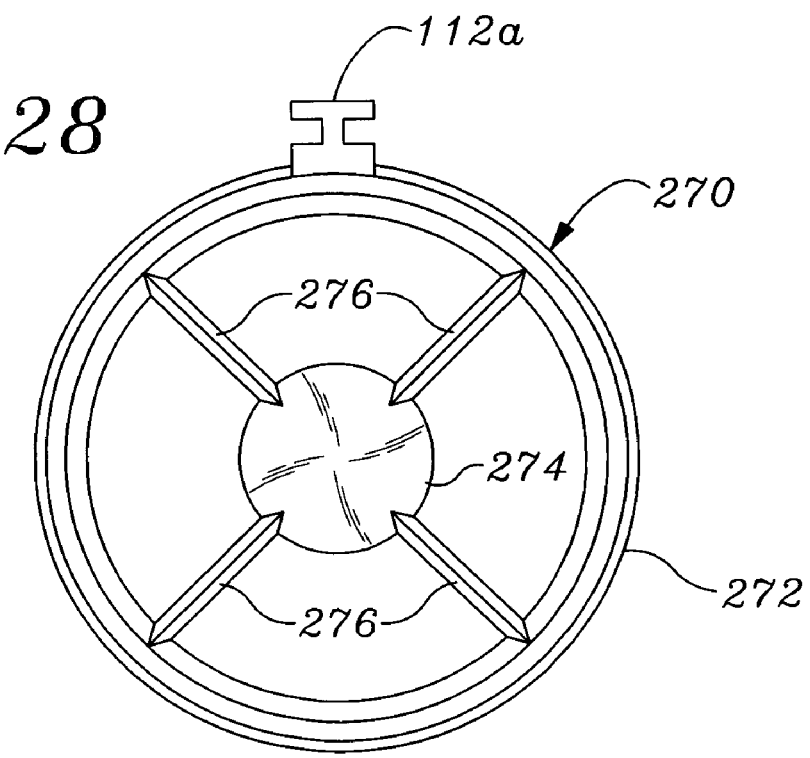
FIG. 28 is a top view of the optional flow diverter of FIG. 27, showing construction thereof.

In the vertical cross sectional drawing of FIG. 23, which is similar to FIG. 22, but represents a subsequent operational stage of dual-chamber device 100a, liquid 250, such as a patient's urine, is shown being discharged into upper chamber 142 of device body 102, lower chamber 144 being shown already filled with the liquid (urine) which has caused float 180 to push orifice stopper 160 upwardly so that stopper region 162 is pushed into sealing relationship with orifice 146, whereupon the liquid has then started filling upper chamber 142. Assuming that device 100a is used for the collection of a patient's urine for bacteriological analysis, urine 252 contained in lower chamber 144 should constitute fore-stream urine, the lower chamber having sufficient volume to assure that urine 254 being collected in upper chamber 142 will constitute uncontaminated midstream urine.

Vertical support column 168 depending from orifice stopper skirt region 164 is telescopically received into the larger diameter guide column 208 extending upwardly from bottom cover 106. The upward movement of orifice stopper 160 is thus perfectly guided and restricted within bottom cover guide column 208.

Orifice stopper locking ring 150 stabilizes stopper sealing region 162 as it is directed into orifice 146 whenever device body 102 is tilted at different angles during its use. Therefore, irrespective of how each patient positions her (or his) device body 102 during the liquid (urine)collection process, the mechanical integrity of the entire dual-chamber device 100 involving fore stream urine capturing, isolation, and precise orifice stopper sealing and closure, always remain constant and intact with the stabilizing action of float 180.

In the vertical cross sectional drawing of FIG. 24, which is similar to FIG. 23, dual-chamber device 100a is shown in its post-use condition with top cover 104 attached to device body 102 and with handle 110 removed from member 112. Device 100a is also shown pressed downwardly onto firm surface 211 so that bottom cover base region 190 and bottom cover extension 220 are fully recessed into device body 102, which causes bottom cover column 210 to push orifice stopper 160 upwardly into tight sealing relationship with orifice 146 with stopper seal 216 forced in a sealing relationship against lower regions of orifice ring 148 and including "latching" stopper locking bead 166 into orifice locking recess 152, and positively locking the stopper into the orifice to assure no liquid leakage occurs between upper and lower chambers 142 and 144. In this condition, colored bottom extension flange 222 will be hidden, thereby providing a visual indication that proper locking has occurred. At times, some nervous and less knowledgeable patients may leave dual-chamber device 100a unlocked. This red colored flange 222 will then be clearly visible to nursing and technician staffs and will immediately remind them to lock device 100a before transporting it to the analysis laboratory.

The over-center locking of bottom cover web 192 which results, locks bottom cover 190 in its upward position shown, thereby securely locking orifice stopper 160 into orifice 146 (as described above) so that regardless of any rough handling of device 100a, no liquid 252 can leak from lower chamber 144 into liquid 254 held in upper chamber 142. Bottom cover locking ring 108, with installed seal 114, prevents liquid leakage at the periphery of bottom cover 106 that might occur if device 100a is not pressed squarely down onto surface 211 during the above-described locking process. As bottom cover base 190 with bottom cover extension 220 attached thereto are retracted upwardly, as above described, bottom cover extension peripheral latching region 226 flexes downwardly to bypass bottom cover locking ring radial projections 241 adjacent central opening 240 and then projects outwardly thereover to help maintain bottom cover web 192 in its over-center locked condition.

Assuming lower chamber liquid 252 is fore-stream urine and upper chamber liquid 254 is mid-stream urine, the upper chamber mid-stream urine would be used for bacteriological analysis, and device 100a still containing lower chamber fore-stream urine would then be discarded.

In some situations it may, however, be necessary or desirable to have access to urine 252 in lower chamber 144 after orifice stopper 160 (and variations thereof) has been locked into orifice 146, as described above. For example, when testing for drugs in an individual's urine it may be necessary, or required by law, to retain, in a tamperproof manner, a reserve or second portion of the individual's urine specimen. A spot drug test would be performed on urine 254 obtained from upper chamber 142, and the second urine 252 portion would be held locked (as described above) in lower chamber 144 until needed to verify the spot drug test results, should they be disputed or require verification.

However, after orifice stopper 160 is locked into orifice 146 as described above, the stopper cannot be unlocked from the orifice without destroying device 100a. Therefore for drug testing use of dual-chamber device 100a (and other dual-chamber device variations, described herein), as depicted in FIGS. 25 and 26, outer wall 138 of device body 102 in the region of lower chamber 144 would have installed therein a self-sealing syringe access port 260 covered by a detachable metal or hard plastic protective cap 262 which is swaged or heat sealed in place. As shown in FIG. 26, after protective cap 262 is removed, it cannot be manually reattached, thereby assuring a tamper-proof specimen in lower chamber 144 and providing a visual indication that urine 252 in lower chamber 144 may already been accessed or possibly treated in some manner so as to adversely affect any drug testing of the urine. A syringe needle 264 is then inserted through port 260 and an attached syringe 266 is used to withdraw from lower chamber 144 a quantity of urine 252 that may be used for secondary drug testing.

Second Variation Dual-Chamber Device 100b:

The present inventors have determined that in some situations wherein a strong, torrential flow of liquid 250 (for example, urine discharged from a female patient) into device upper chamber 142 and impinging on orifice stopper 160 may possibly cause cocking of the stopper to the extent that proper orifice sealing is hindered when the stopper is floated up into orifice 146. As a result, it is within the scope of the present invention to provide a flow diverting and sanitary barrier adapter 270, as shown in FIGS. 27–31 and which comprises part of a second variation dual-chamber device 100b.

Shown comprising flow diverting and sanitary barrier adapter 270 are a peripheral mounting ring 272 and a central dome 274 supported from the mounting ring by equally spaced apart, slender, downwardly-angled beams 276 (four such beams being shown). A handle attachment fitting 112a is fixed to mounting ring 272 for receiving handle 110.

Figure 29:
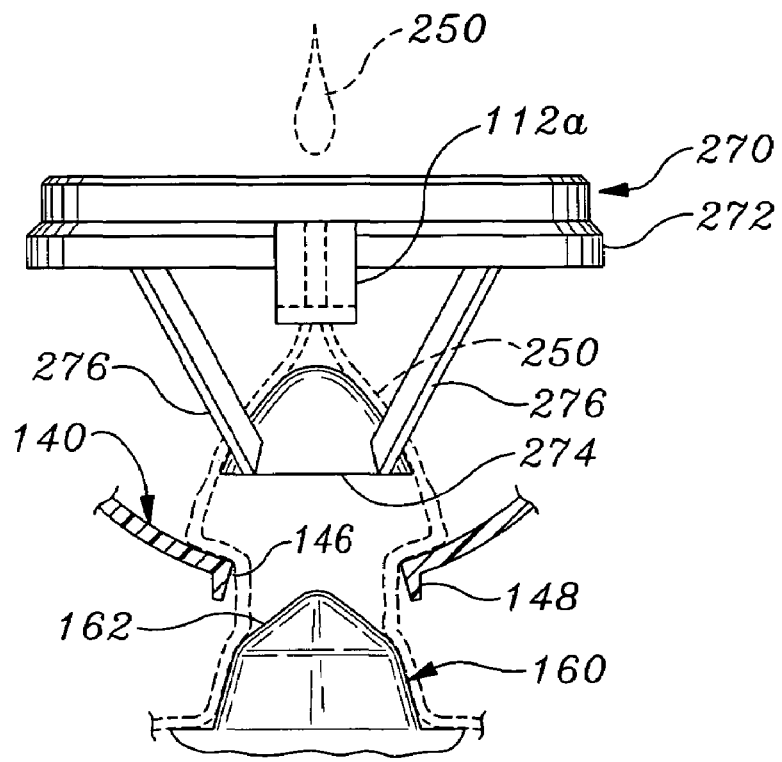
FIG. 29 is a side view of the optional flow diverter of FIG. 26, showing construction thereof and showing the liquid diverter in relationship to upper, orifice sealing regions of the stopper, and further depicting the diverting of a flow of liquid past the diverter dome onto the sloping transverse inner wall.
Figure 30:
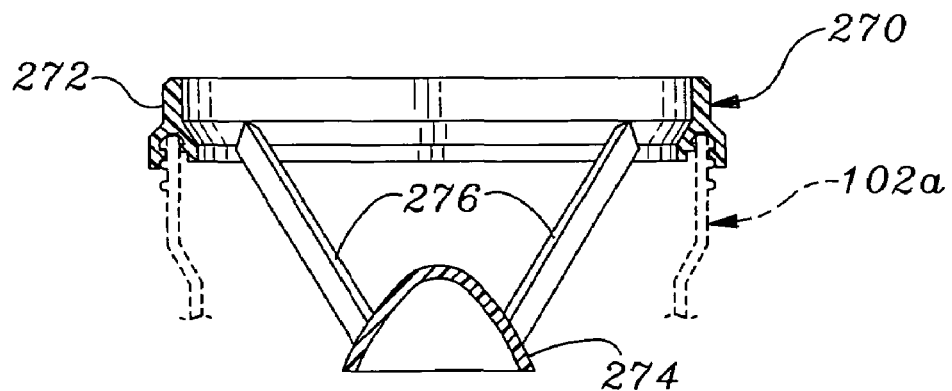
FIG. 30 is a side view of the optional flow diverter similar to FIG. 29, but showing the liquid diverter detachably attached to the open top of a representative device body.

As shown in FIG. 29, when flow diverting and sanitary barrier adapter 270 is snapped onto the upper edge of device body 102a, central dome 274 is located directly above orifice 146 and stopper 160. As depicted, an introduced urine flow 250 (shown in broken lines) flows downwardly around dome 274 and then onto transverse wall 140 and then downwardly onto side regions of stopper 160, the liquid flow being thereby reduced in force onto the stopper.

Figure 31:
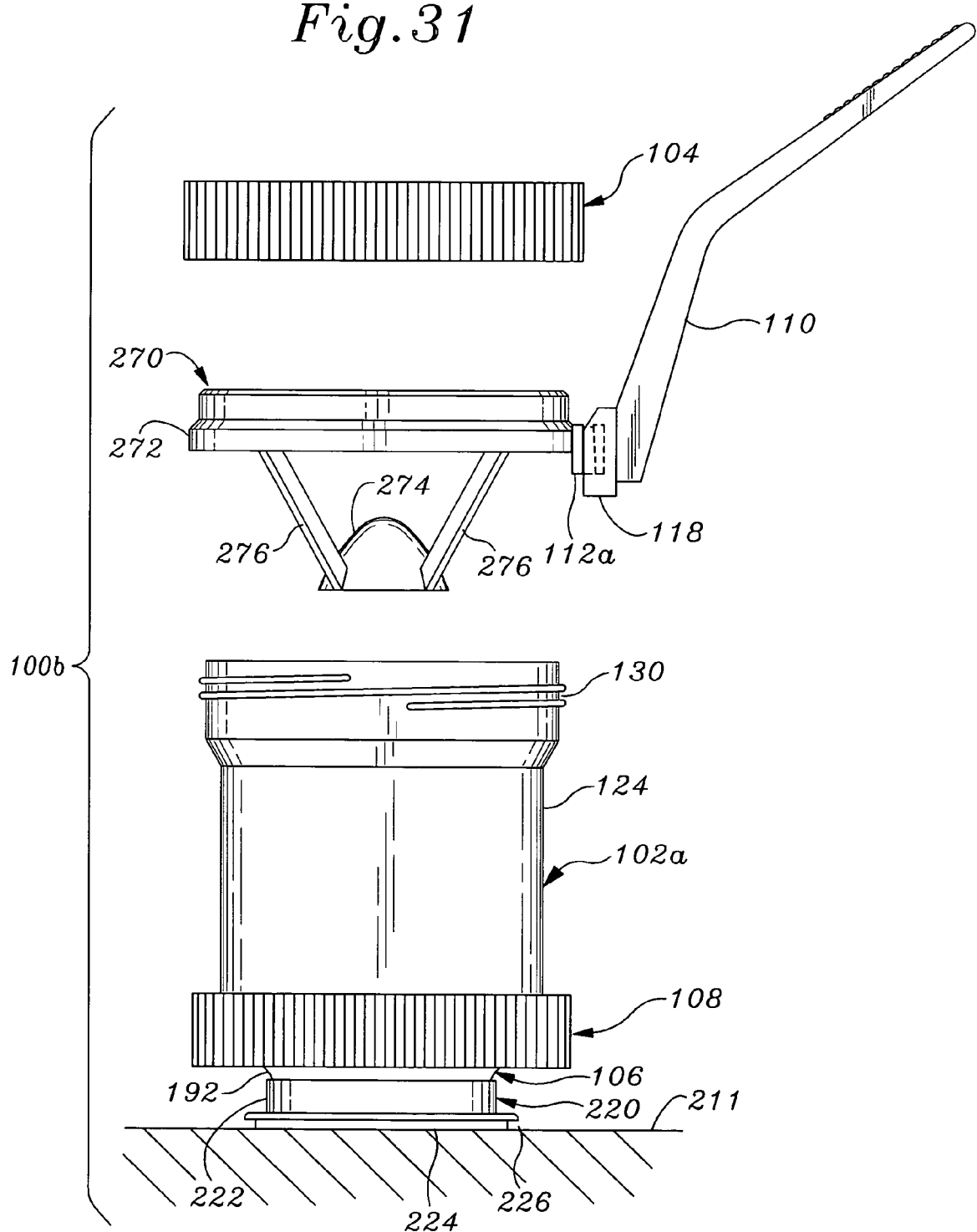
FIG. 31 is an exploded elevational drawing, similar to FIG. 18, of a second variation dual-chamber device to which the flow diverter of FIGS. 27–30 is positioned for detachable attachment.

Second variation dual-chamber device 100b is depicted in FIG. 31, showing handle 110 detachably attached to fitting 112b formed on diverter mounting ring 272. Except for sanitary barrier adapter 270 with attached handle 110, and except that device body 102a does not have handle fitting 112 attached thereto, dual-chamber device 100b is the same as above-described device 100a and is internally constructed and operates in the above-described manner of device 100a. After liquid has been discharged into body 102a, adapter 270 with attached handle 110 is removed from device body 102a and is discarded. Adapter 270 also provides a sanitary barrier to maintain sterility of body 102a against accidental contamination by contact with the patient's unclean external body regions. Top cover 104 is then threaded onto device body 102a to seal device 100b for subsequent urinalysis.

Third Variation Dual-Chamber Device 100c:

It will be appreciated that a locking of orifice stopper 160 into orifice 146 (as described above for devices 100, 100a and 100b) in a more automatic manner will, at least in some circumstances, be more desirable than the mechanical locking method described above which requires manually pushing down on dual-chamber device 100 or 100a to flex bottom cover web 192 into its over-center locking condition.

Figure 32:
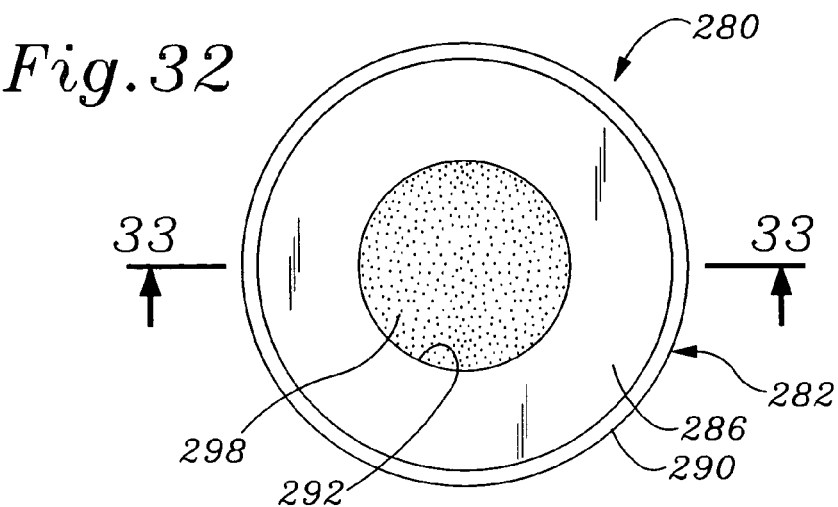
FIG. 32 is a top view of an automatic, spring-loaded orifice stopper locking assembly, showing a cylindrical housing having an partially open top with a liquid-softening, compressed spring retaining element positioned just beneath the partially open top.
Figure 33:
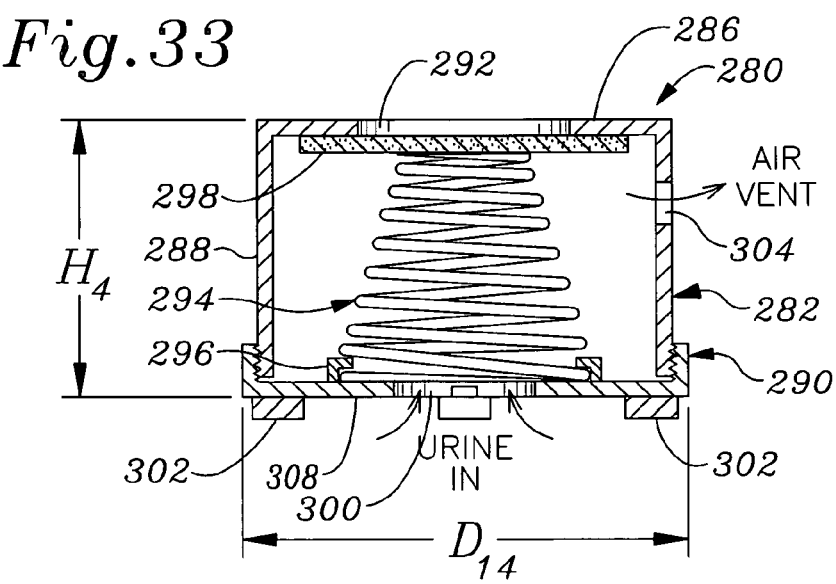
FIG. 33 is a vertical cross sectional drawing taken along line 33–33 of FIG. 32, showing a conically shaped spring attached inside a bottom of the housing and held in a compressed condition by the spring retaining element, and showing a side air vent and a bottom liquid inlet.
Figure 34:
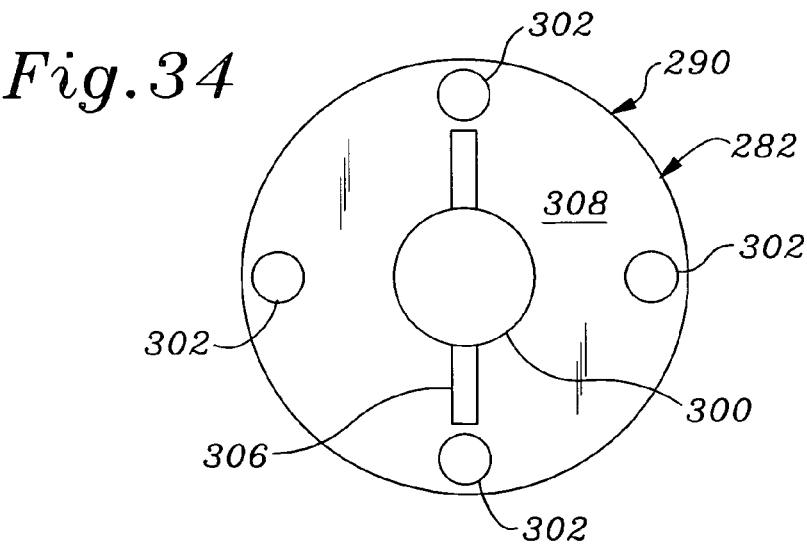
FIG. 34 is a bottom view of the housing of FIG. 33, showing the liquid inlet and showing a slotted region provided for assisting threaded attachment of the bottom to sides of the housing.
Figures 35, 36:
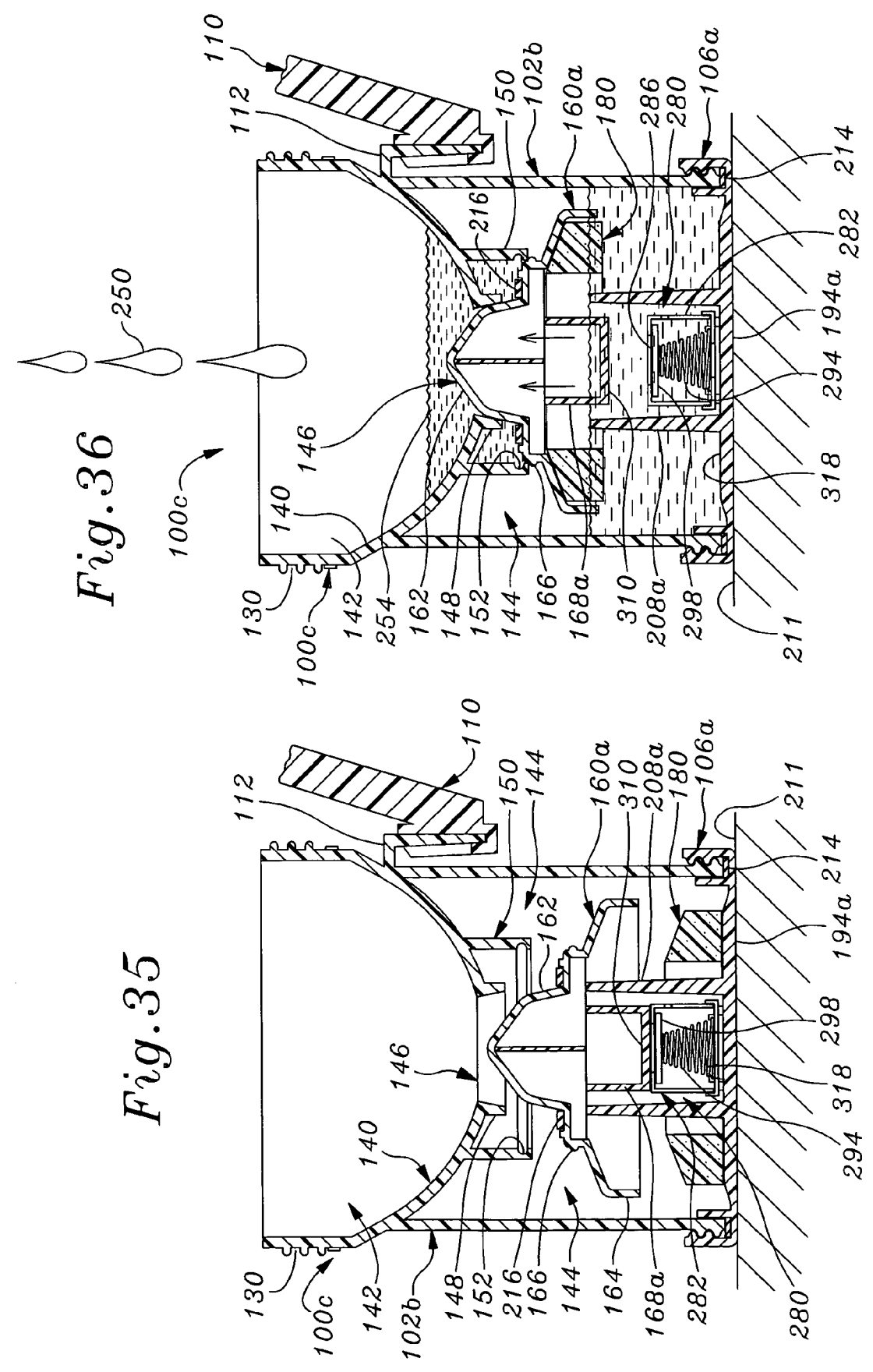

To this end, there is disclosed in FIGS. 32–38 a spring-type orifice stopper locking assembly 280 for a third variation dual-chamber device 100c (FIGS. 35–37). As shown, locking assembly 280 comprises a relatively small, preferably cylindrical, housing 282 which includes an upper member 284 having a top 286 and a cylindrical side wall 288. A housing base 290 is threaded upwardly onto the bottom of side wall 288 (FIGS. 32–33). Housing 282 has a height, $H_4$, that may be about 0.31 inch.

As best seen from FIG. 33, a relatively large, centrally-located aperture 292 is formed in housing top 286. A conically-shaped compression spring 294 is retained inside housing 282 by a circular member 296 fixed to housing base 290, and is maintained in its compressed condition by a rigid, aqueous liquid-softenable, spring-retaining disc 298, which may be formed from a suitable fiber material, such as cardboard, that is positioned above compressed spring 294 and directly beneath top aperture 292.

Housing base 290, which has a diameter, $D_{14}$, that may be about 0.63 inch, is formed with a central liquid entry aperture 300 and having a plurality of small, short feet 302 that space locking assembly 280 upwardly from device bottom cover 106a so that liquid (urine) collected in lower chamber 144 can enter housing 282 through base aperture 300 to soften spring-retaining disc 298 and release the compression of spring 294. An air vent 304 is provided in housing side wall 288. A groove 306 is provided in base lower surface 308 (FIG. 34) to receive a screw driver blade for facilitating screwing housing base 290 onto housing side wall 288.

Shown in vertical cross section in FIGS. 35–37 third variation dual-chamber device 100c incorporates above-described spring-type orifice stopper locking assembly 280.

Shown further comprising dual-chamber device 100c is a device body 102b, a bottom cover 106a, an orifice stopper 160a, float 180 and handle 110. Dual-chamber device 100c, for reasons described below, eliminates bottom cover locking ring 108 as unnecessary.

Device body 102b is shown identical in all respects to above-described device body 102, except that a lower threaded region 132a is formed directly above a lower end of the device body for the threadable attachment of bottom cover 106a.

Orifice stopper 160a is identical in all respects to above-described orifice stopper 160 except that depending column 170a is shorter than column 170 shown in FIGS. 7 and 8, and is closed at a lower end 310. Bottom cover 106a is similar to above-described bottom cover 106 (FIGS. 13–17), except that annular web 192 is eliminated, permitting a base 194a to be entirely flat and extend entirely across device body 102b, and is formed having a peripheral internally threaded attachment region 312 that mates with device body threaded region 132a upon assembly of dual-chamber device 100c.

As shown in FIGS. 35–37, compressed spring orifice stopper locking assembly 280 is attached to an upper surface 318 of bottom cover 106a inside column 208a and directly beneath orifice stopper closed lower end or bottom 310. Column 208a is formed having a plurality of vertical slits (not shown) to allow aqueous liquid access to locking assembly 280 and disc 298.

In the pre-use condition of dual-chamber device 100c, depicted in FIG. 35, orifice stopper 160a is resting on top 286 of locking assembly housing 282, and float 180 is resting on bottom cover upper surface 318.

As depicted in FIG. 36, which corresponds to FIG. 35, but represents a subsequent operation or use stage of dual-chamber device 100c, liquid (urine) is being introduced into dual-chamber device 100c, having filled lower chamber 144 to the extent that orifice stopper 160a has been floated upwardly into sealing engagement with orifice 146, and upper chamber 142 has subsequently been partially filled with liquid (urine) 154. At this depicted point in time, spring retaining disc 298 has not yet been sufficiently softened by aqueous liquid 152 in lower chamber 144 to release locking spring 294 from its shown compressed state.

Preferably at least about 20 seconds of immersion in aqueous liquid (urine) is required to soften spring retaining disc 298 sufficiently for it to release spring 294, which allows sufficient time for orifice stopper 160a to be floated upwardly into orifice 146 to stop liquid flow into lower chamber 144. This softening of spring-retaining disc 298, releases spring 294 which then expands and pushes the disc upwardly through housing opening 296 and expands further to push orifice stopper 160 upwardly into tight sealing relationship with orifice 146 with stopper seal 216 forced in a sealing relationship against lower regions of orifice ring 148, and including "latching" stopper locking bead 166 into orifice locking recess 152, and positively locking the stopper into the orifice to assure no liquid leakage occurs between upper and lower chambers 142 and 144, as depicted in FIG. 37. FIG. 38 is an enlargement of region 38 of FIG. 37 depicting the above-described actuation of spring-type orifice stopper locking assembly 180.

It will be appreciated that the above-described tight locking of orifice stopper 160a into orifice 146 by orifice stopper locking assembly 280 is completely automatic and operates solely in response to liquid (urine) 154 filling device body lower chamber 144 without requiring any manual intervention.

Fourth Variation Dual-Chamber Device 100d:

A fourth dual-chamber device 100d is depicted in FIGS. 39–40 which utilizes a quantity or element of highly expandable, hydrophilic material capsule or element 330 to provide automatic locking of above-described orifice stopper 160a into orifice 146, the process being otherwise similar, and comparable, to that described above for spring-type orifice stopper locking assembly 280 (FIGS. 35–38).

As shown in the vertical cross sectional pre-use drawing of FIG. 39, expandable, hydrophilic material capsule or element 330 is disposed within orifice stopper column 170 above bottom cover 106a and in contact with a transverse stopper closing member 332. Orifice stopper column 168a rests on hydrophilic material capsule 330 and float 180 is resting on bottom cover upper surface 318 of bottom cover 106a.

As depicted in the vertical cross sectional post-use drawing of FIG. 40 (which corresponds to FIG. 39), as aqueous liquid (urine) 252 fills lower chamber 144, the liquid flows through above-described openings in column 208a and contacts hydrophilic material capsule 330 causing the material to greatly expand (swell), thereby exerting an upward force on stopper bottom 310 to push orifice stopper 160 upwardly into tight sealing relationship with orifice 146 with stopper seal 216 forced in a sealing relationship against lower regions of orifice ring 148, and including "latching" stopper locking bead 166 into orifice locking recess 152, thereby positively locking the stopper into the orifice to assure no liquid leakage occurs between upper and lower chambers 142 and 144

Again, as in the case of the spring-type orifice stopper locking assembly 280, the use of expandable, hydrophilic material capsule 330, provides for the automatic locking of orifice stopper 160b into orifice 146 solely in response to liquid (urine) 154 filling device body lower chamber 144 without requiring any manual intervention.

Fifth Variation Dual-Chamber Device 100e:

A fifth variation dual-chamber device 100e is depicted in FIGS. 41–43. Dual-chamber device 100e utilizes a gas generator assembly 340 comprising an aqueous liquid-activated effervescent tablet or element 342 disposed in a cylindrical tablet housing 344 to achieve automatic locking of orifice stopper 160b into orifice 146. Dual-chamber device 100e is similar in many respects to both above-described dual-chamber devices 100c and 100d.

As shown in the vertical cross sectional drawings of FIGS. 41–44 gas generator assembly 340 is installed in dual-chamber device 100e within orifice stopper column 168b and is attached to bottom cover upper surface 318. As shown in the pre-use condition of FIG. 41, orifice stopper column 168b is resting on bottom cover upper surface 318, as is float 180.

Shown in detail in FIG. 42, gas generator assembly tablet housing 344 includes a top 350, a cylindrical side wall 352 and a bottom 354. Housing bottom 354 is formed having a plurality of small, short feet 356 that space gas generator assembly 340 upwardly from device bottom cover upper surface 318 so that liquid collected in lower chamber 144 can enter through above-described slits in bottom cover column 208a and then through holes 358 formed in housing bottom 354 to activate effervescent tablet 342. Holes 360 are provided in housing top 350 to enable generated gas bubbles 362 to escape from housing 344 (FIGS. 43 and 44). A hole 366 is formed in housing side wall 352 to enable the escape of air from housing 344 during initial activation of effervescent tablet 342.

As depicted in the vertical cross sectional drawing of FIG. 43, gas bubbles 362 rising from gas generator 340 pushs orifice stopper 160 upwardly into tight sealing relationship with orifice 146 with stopper seal 216 forced in a sealing relationship against lower regions of orifice ring 148, and including "latching" stopper locking bead 166 into orifice locking recess 152, thereby positively locking the stopper into the orifice to assure no liquid leakage occurs between upper and lower chambers 142 and 144. Similarly to above-described dual-chamber devices 100c and 100d, the generated gas locking of orifice stopper 160b into orifice 146 is accomplished when lower chamber 144 is filled with aqueous liquid (urine) 152 and without any manual intervention.

Sixth Variation Dual-Chamber Device 100f:

A sixth variation dual-chamber device 100f, shown in FIGS. 45–49, comprises device body 102b, an orifice stopper 160c, a bottom cover 106b, an orifice stopper pushing base 380 and a very soft removable sponge element 382 disposed between the bottom cover and the stopper pushing base.

Shown in FIGS. 45 and 47 comprising bottom cover 106b are a centrically-located, upwardly extending, lower tubular portion 384, which is open at the bottom and which terminates in a smaller diameter, upwardly-extending upper tubular region 386. Otherwise bottom cover 106b is the same as above-described bottom cover 106a.

Orifice stopper 160c is formed having a slender, central, depending tubular pushing pin guide 388 which fits closely into bottom cover upper tubular region 386. Orifice stopper 160c rests, in the pre-use condition of dual-chamber device 100f on an upper end region 390 of bottom cover lower tubular region 384 (FIG. 45). Otherwise, orifice stopper 160c is substantially the same as above-described orifice stopper 160a.

Pushing base 380 is formed having a flat bottom 392 with a centrally-located, upwardly-extending column 394 which fits closely into bottom cover lower tubular region 384. Extending upwardly from a top 396 of column 394 is an elongate slender orifice stopper pushing pin 400 which extends upwardly in a close-fitting relationship through orifice stopper pin guide 388. As shown in FIG. 45, top 396 of pushing base column top 396 is spaced substantially below upper end region 390 of bottom cover lower tubular region 384. Pushing base 380 is formed having a recessed; well region 402 surrounding column 394 into which sponge element 382 is received, the recessed region being further defined by a peripheral attachment flange 406 configured for snapping upwardly onto bottom cover 106b, as shown in FIG. 47. Peripheral attachment flange 406 extends about 270 degrees around pushing base 380 (FIG. 29) to provide suitable space for withdrawing of sponge element 382 from the pushing base, as described below.

As shown in FIG. 46, sponge element 382 has a central diameter, $D_{15}$, that may be about 0.08 inch, so as to fit loosely around column 394 and a height, $H_5$, that may be about 0.4 inch. A relatively wide gap 410 is formed in sponge element 382 to permit withdrawal of the element from pushing base recessed region 402. A thin, projecting finger tab 412 is joined to sponge element 382 opposite gap 410. Before liquid (urine) is introduced into device 100f, sponge element 382 is withdrawn from pushing base recess 402 and is discarded. Friction between column 394 and tubular region 384 retains pushing base 380 in its pre-sponge removal condition until liquid (urine) filled device 100f is subsequently set onto surface 211, as described below.

The use of dual-chamber device 100f is evident from FIGS. 47–48. As liquid (urine) fills device lower chamber 144, orifice stopper 160c is floated upwardly into a sealing relationship with orifice 146, whereupon liquid (urine) is collected in device upper chamber 142. After liquid (urine) 152 is collected in lower chamber 144 and liquid (urine) 154 is collected in upper chamber 142 is set on surface 211. The weight of the liquid (urine) 152 and 154 in device body 102b, then causes the device body with bottom cover 106b to settle downwardly into pushing base recess 402, thereby causing pushing pin 400 to push upwardly against orifice stopper 160c in a manner pushing the orifice stopper 160 upwardly into tight sealing relationship with orifice 146 with stopper seal 216 forced in a sealing relationship against lower regions of orifice ring 148, and including "latching" stopper locking bead 166 into orifice locking recess 152.

Subsequent to such downward settling of device body 102b, cover 104 is installed on the device body and device 100f is manually pressed downwardly on surface 211 to cause pushing base peripheral flange 406 to snap up over the bottom cover periphery to retain pushing base 380 onto bottom cover 106b. This positively locks stopper 160c into orifice 146 and device 100f can then be handled (even carelessly) without the possibility of the stopper being dislodged from the orifice and causing liquid (urine) 152 to leak past the orifice stopper between upper and lower chambers 142 and 144.

Seventh Variation Dual-Chamber Device 100g:

A seventh variation dual-chamber device 100g, shown in FIGS. 50–52, provides a magnetic locking of orifice stopper 160d into orifice 146 in the manner described below. As shown in FIG. 50, above-described orifice stopper 160d, which corresponds to above-described orifice stopper 160b (FIG. 41) is formed having a magnetic member 420 attached (as by cementing) to and around an under surface 422 of stopper skirt 164. Magnetic member 420 may constitute a single-piece, annular magnet or may comprise two or more magnetic segments. A corresponding magnetic member 424 is attached to an outer surface 426 of orifice locking ring 150 spaced above stopper magnetic member 420.

A removable soft-type sponge spacer 430 is shown in FIG. 50 initially installed in dual-chamber device body 102b between locking ring magnetic member 424 and orifice stopper 160d to keep magnetic members 424 and 420 separated before use of device 100g. Forming spacer 430 is a conically-shaped separation region 432 to which is joined a finger tab 434. Initially orifice stopper 160d rests on bottom cover 106a, as does float 180.

When, as depicted in FIG. 52, spacer 430 is removed from device body 102b and orifice stopper 160d is floated upwardly into engagement with orifice 146 by liquid (urine) 152 collected in lower chamber 142, magnet members 424 and 420 attract each other, thereby drawing the orifice stopper tightly into orifice 146 with stopper seal 216 forced in a sealing relationship against lower regions of orifice ring 148 and with stopper locking bead 166 "latched" into orifice locking recess 152, thereby positively locking the stopper into the orifice to assure no liquid leakage occurs between upper and lower chambers 142 and 144.

Eighth Variation Dual-Chamber Device 100*h*:

An eighth variation dual-chamber device 100*h*, shown in FIGS. 53–56, provides locking of orifice stopper 160 into orifice 146 by a liquid-activated cementing process in the manner described below. As shown in the pre-use condition of FIG. 53, dual-chamber device 100*h* comprises device body 102*c*, orifice stopper 160, float 180 and bottom cover 106*a*. Orifice stopper 160 and float 180 are shown resting on bottom cover 106*a* below orifice 146. A coating 440 of an aqueous liquid (urine) activated cement (adhesive) is applied to and around inner surface 442 of orifice ring 148 (also FIG. 54), and is initially protected by a flexible, removable "release" 444, which may be made from waxed paper or plastic material.

As shown in the post-use condition of FIGS. 55 and 56, "release" 444 has been withdrawn from orifice ring 148 to expose cement coating 440 to, and be activated by, liquid (urine) flowing into device body 102*b*. As liquid 252 is collected in lower chamber 144, orifice stopper 160 is floated upwardly into sealing engagement with orifice 146, thereby contacting activated cement coating 440, which then cements the orifice stopper into orifice ring 148. This causes orifice stopper 160 to be permanently locked and strongly sealed into orifice ring 148, thereby preventing any leaking of liquid 252 between upper and lower chambers 142 and 144, regardless of any subsequent handling or mishandling of dual-chamber device 100*h*.

Summary of Use of Exemplary Dual-Chamber Device 100*a*:

The operational use of exemplary dual-chamber device 100*a* is depicted step-wise in FIGS. 57A–57H. When a patient with a unclean or poorly clean anatomic part uses device 100*a*, the earlier fore-stream urine volume (40 to 70 ml) is regarded as favorably useful because, it helps to flush, rinse and clean the external urogenital tract, which extends from the urethra to device 100*a*. Such flushing and rinsing mechanism creates a cleaner tract for the subsequent mid-stream sample flowing through this same tract into dual-chamber device 100*a*. Thus, (referring to FIGS. 22–24) dual-chamber device 100*a* has the ability to capture the earlier "rinsing" contaminated fore-stream urine and isolate it in separate lower chamber 144. Dual-chamber device 100*a* will then continue to collect the later cleaner mid-stream sample in upper chamber 142, which is separated from lower chamber 144 by orifice stopper 160. This separation and isolation renders dual-chamber device 100*a* completely free from mixing the contaminated fore-stream sample with the clean mid-stream sample. (The foregoing applies to all above-described dual-chamber devices 100 and 100*b*–100*h*).

Figure 57A:
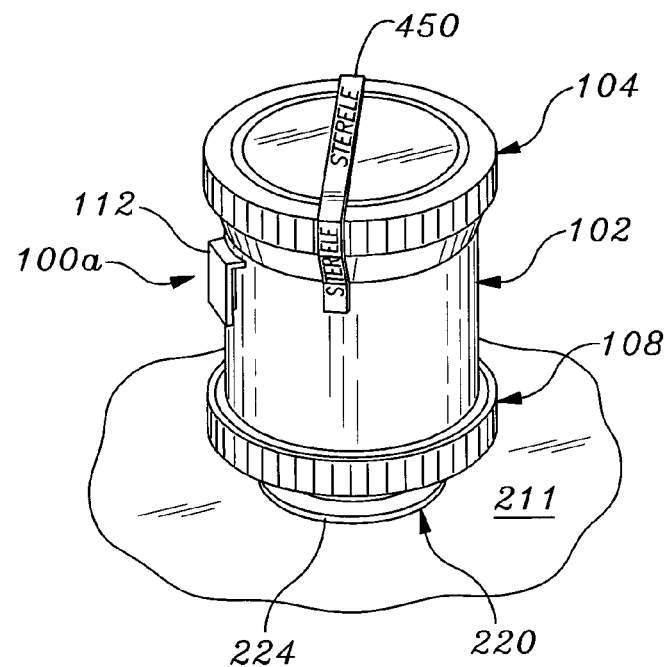
FIG. 57 is a series of diagrams depicting a number of steps showing operational use of the dual-chamber device of FIGS. 19–24, FIG. 57A showing the dual-chamber device assembled as depicted in FIG. 20, except the handle is not yet attached and showing the top cover sealed with a sterile-evident tape identifying the device as "STERILE"
FIG. 57B depicting the handle about to be attached to the dual device body.
FIG. 57C depicting the handle being upwardly attached to the dual device body.
FIG. 57D depicting removal of the top cover tape.
FIG. 57E depicting a flow of liquid being discharged into the device upper chamber after removal of the top cover.
FIG. 57G depicting the final step of pushing downwardly on the dual-chamber device to lock the stopper in the orifice (as shown in FIG. 24)
FIG. 57H depicting the dual-chamber device in its final, post use condition.

FIG. 57A depicts dual-chamber device 100*a* (minus handle 110) in its assembled, initial, pre-use condition and corresponds generally to above-described FIG. 20. Device body 102 is shown closed by top cover 104 which is, in turn, sealed by a sterile-marked adhesive sealing strip 450 indicating that the device is in a sterile condition. Bottom cover 106 (not shown) is retained by locking ring 108 and rests on bottom extension member 220.

Figure 57B:
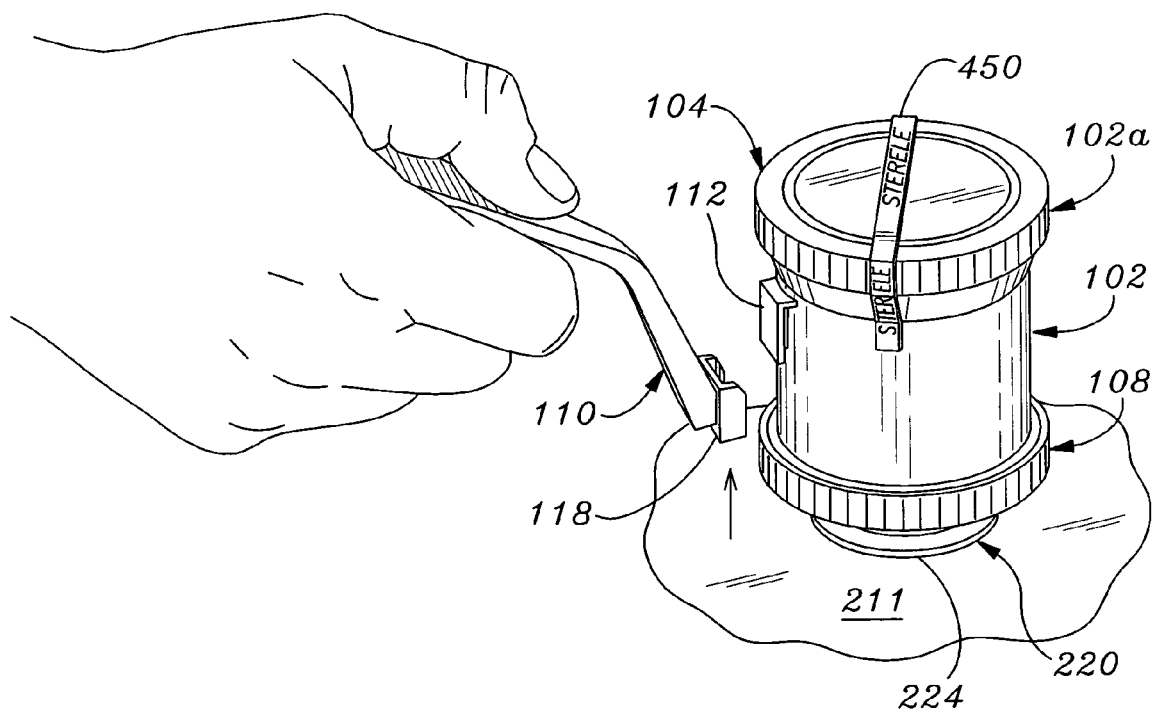
Figure 57C:
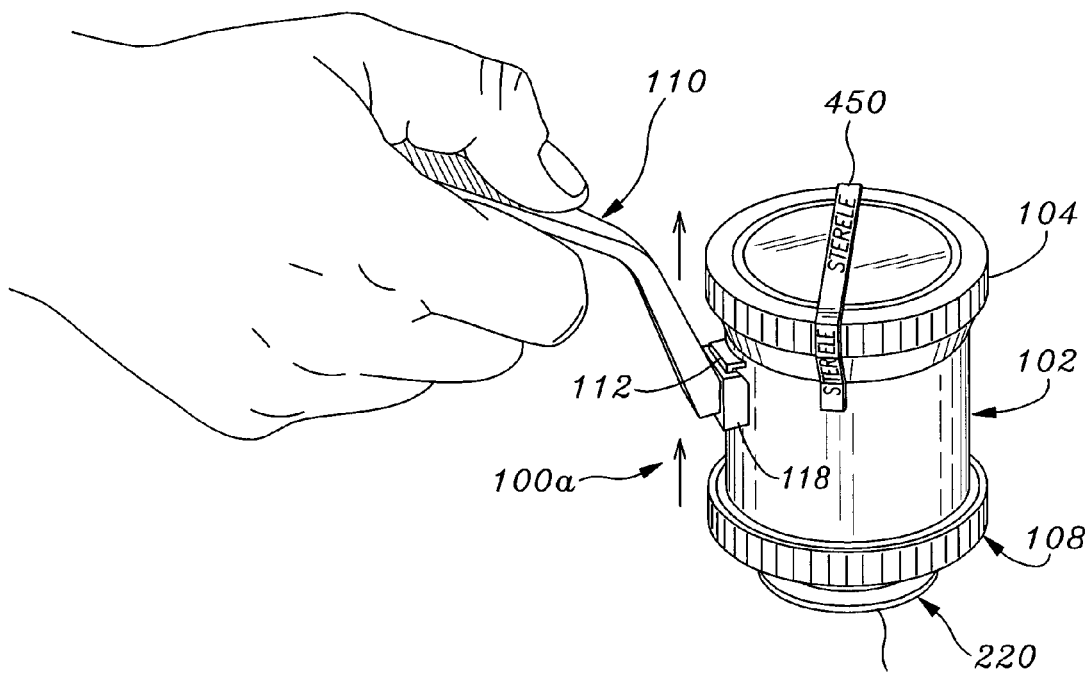
Figure 57D:
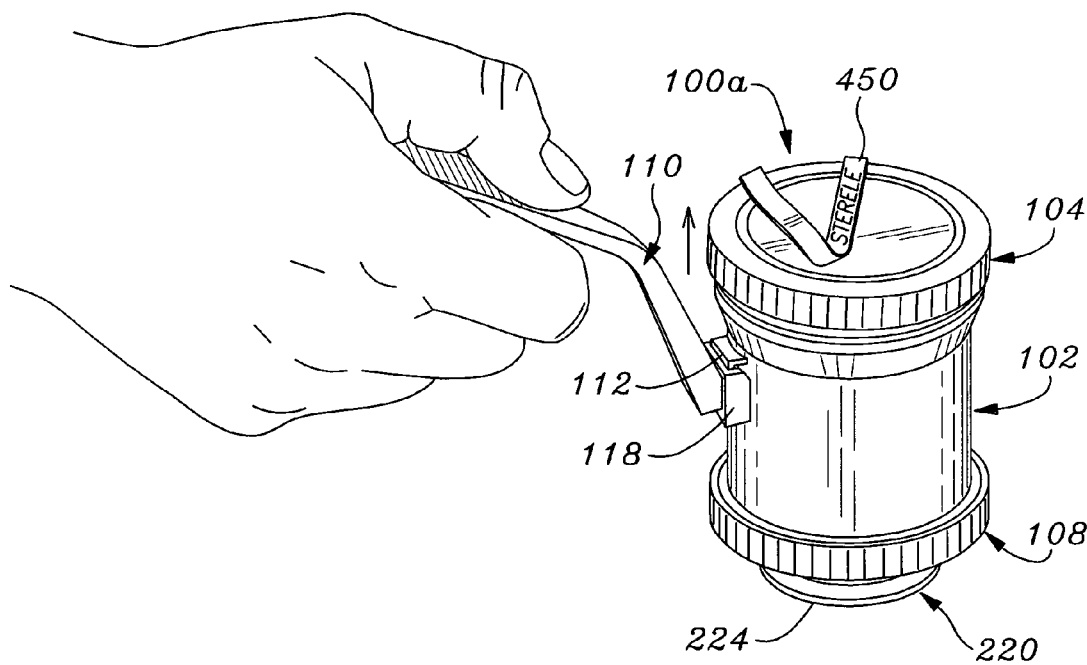

In FIG. 57B, handle 110 is shown being fitted upwardly onto device body fitting 112, with adhesive sealing strip 450 still in place. Handle 110 being shown in FIG. 57C fully received onto device body fitting 112. FIG. 57D shows adhesive sealing strip 450 in the process of being removed and top cover 104 in the process of being unscrewed from device body 102.

Figure 57E:
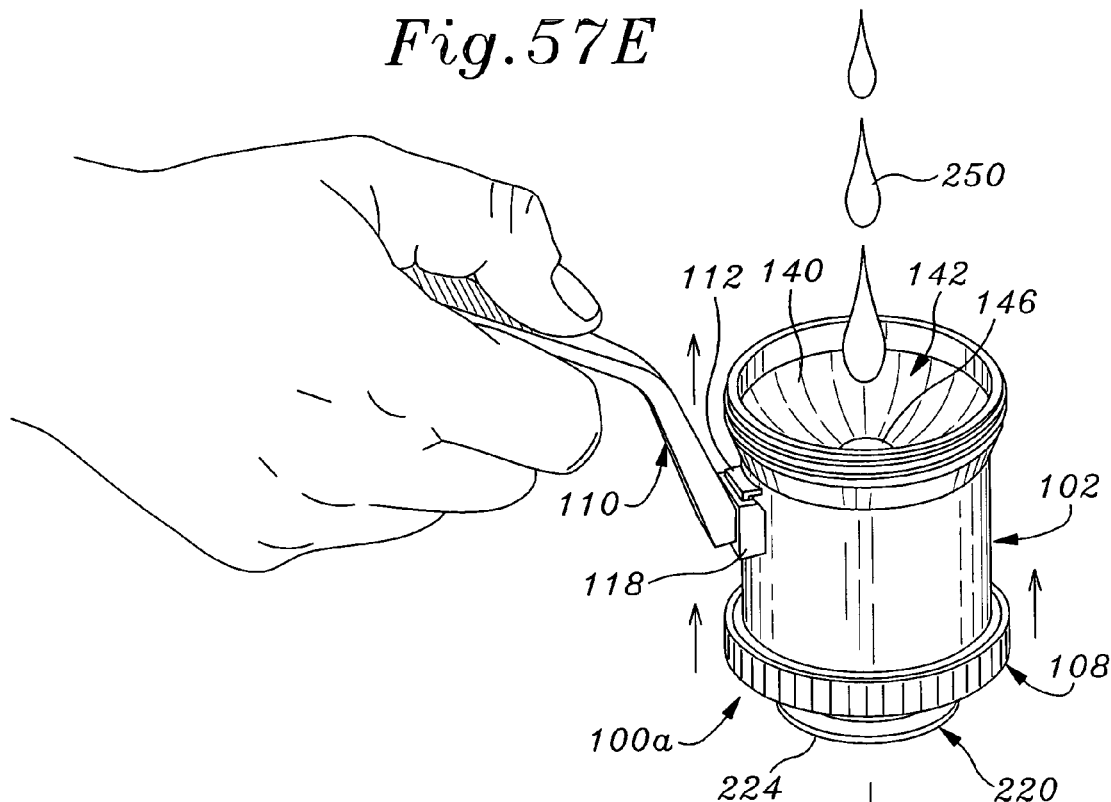

FIG. 57E depicts liquid (urine) 250 being discharged into upper chamber 142 of device body 102, and corresponds to FIG. 22. Although not shown in this FIG., the highly contaminated fore-stream urine first flows into lower chamber 144 through orifice 146 located between it and upper chamber 142 situated directly above, this configuration resembling an hourglass. As soon as the fore-stream urine floods lower chamber 144, it creates an air pocket underneath the orifice stopper skirt region 164. The progressively increased fluid level within lower chamber 144 elevates the orifice stopper sealing region 162, directing it towards orifice 146 to plug off the lower chamber. Simultaneously, stabilizing float 180 floats upwards by buoyancy and further elevates orifice stopper 160, directing it even more forcibly and rapidly towards orifice 146 to close it off. When the fore-stream sample has reached a pre-determined volume of (between 40 to 70 ml), orifice stopper sealing region 164 has already ascended maximally through orifice 146, producing a tight sealing contact between the stopper sealing region and orifice ring 148 to shut off further liquid (urine) inflow into lower chamber 144.

Figure 57F:
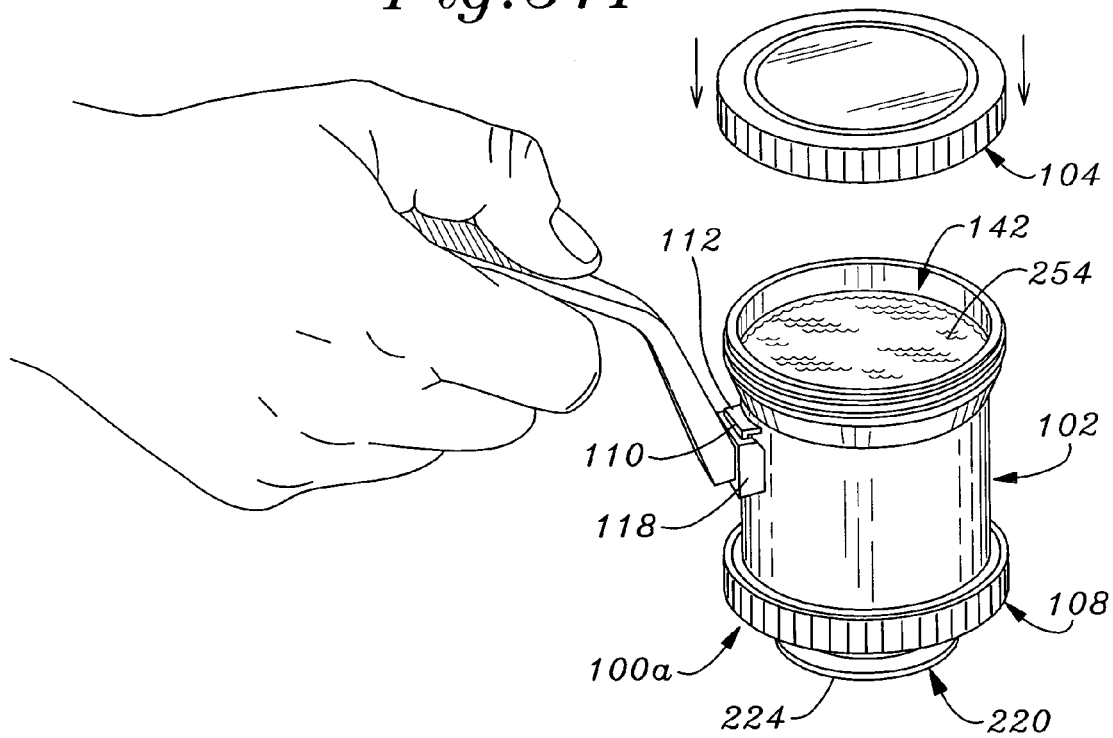

FIG. 57F shows device body upper chamber 142 filled with liquid (urine) 254 and with top cover about to be installed onto device body 102 for the closing thereof. Top cover 104 is screwed onto device body 102, while using handle 110 to steady and counter rotate the device body while the top cover is being screwed onto the device body.

Figure 57G:
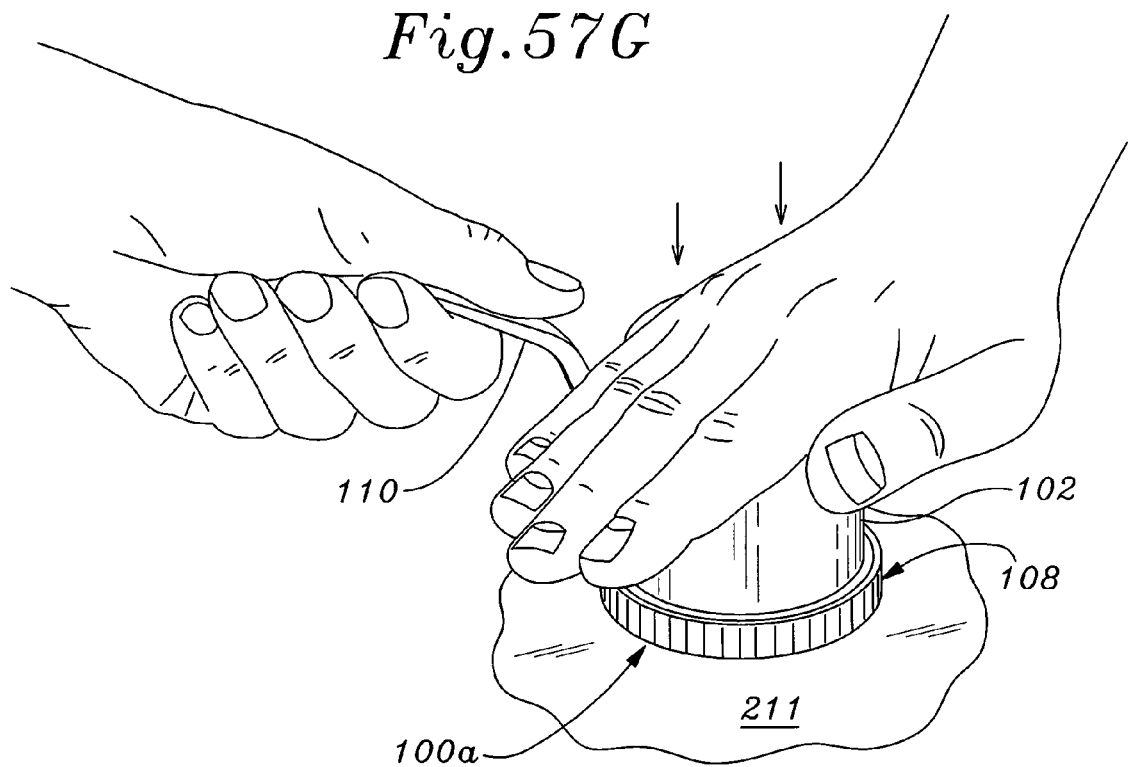
Figure 57H:
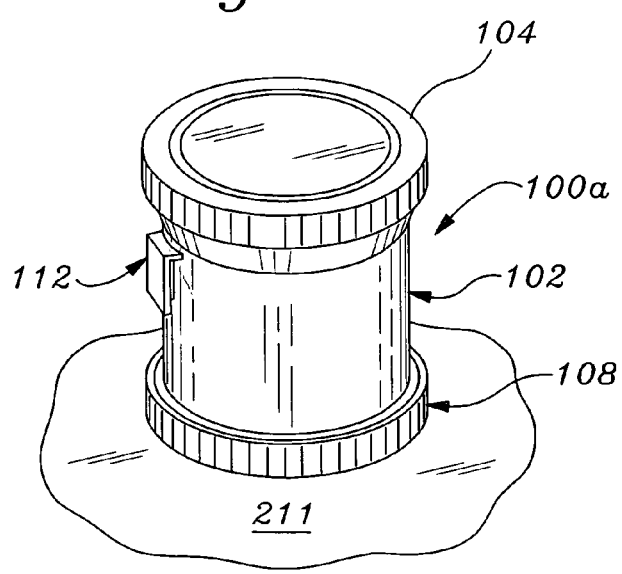

FIG. 57G shows liquid (urine) containing device 100*a* being pressed downwardly onto surface 211 to cause flexing of bottom cover web 192 (not shown) into an orifice stopper locking condition (corresponding to FIG. 24). Finally, FIG. 57H shows dual-chamber device 100*a* in its post-use condition with bottom cover extension member 220 forced upwardly into device body 102 and the red-colored extension member is no longer visible (also corresponding to FIG. 24).

With respect to the foregoing, it is preferred that device body 102*a*–102*d*, handle 110, orifice stopper 160 and 160*a*–*d*, top cover 104, bottom cover locking ring 108, bottom cover 106*a*–*b*, bottom cover extension 220, secondary bottom cover 380, and sanitary barrier adapter 270 each be constructed of a rigid plastic material, such as the high density polyethylene plastic as disclosed above as preferred for device body 102.

Thus, there has been described above a dual-chamber device for collecting and storing liquid samples (specifically urine samples) and several variations thereof for purposes of illustrating the manner in which the present invention may be used to advantage. It will, however, be appreciated that the invention is not limited thereto but includes any and all variations and modifications which may occur to those skilled in the art without violating the scope and spirit of the claims as appended hereto.

What is claimed is:

1. A dual-chamber liquid receiving and retaining device which comprises:
   a. a liquid receiving and retaining body, said body having a continuous outside wall, and an open top and an open bottom;
   b. a detachable top cover and a detachable bottom cover for said body;
   c. a funnel-shaped transverse inner wall dividing said body into an upper liquid receiving and retaining chamber and a lower liquid receiving and retaining chamber, said transverse inner wall tapering downwardly toward a transverse inner wall orifice which enables liquid flow communication between said upper and lower chambers;

d. an annular depending locking flange surrounding said orifice, said flange being formed having a narrow inner annular locking recess; and e. an orifice stopper disposed in said lower chamber, said stopper being responsive to liquid filling said lower chamber to a predetermined level for causing the stopper to float upwardly into sealing engagement with said orifice for preventing liquid flow into the lower chamber, said stopper being formed having a narrow external annular bead shaped to latch into said locking flange annular recess when the stopper is tightly received into said orifice; and f. an annular, spring-like flexible web formed in said bottom cover and responsive to a downward pushing on the device for deflecting upwardly in a manner causing a central upstanding region of the bottom cover to engage said stopper and force the stopper upwardly into said orifice and latch said stopper external annular bead into said locking flange annular recess for tightly sealing the orifice against liquid leakage past the stopper.

2. The dual-chamber device as claimed in claim 1, wherein when said web is upwardly deflectable to cause said bottom cover upstanding region to force the stopper tightly into said orifice and latch said stopper external annular bead into said locking flange annular recess, the web being lockable over-center to positively lock the stopper into the orifice and latch said stopper external annular bead into said locking flange annular recess so as to assure that liquid does not leak past the stopper between said upper and lower chambers.

3. The dual-chamber device as claimed in claim 2, including a bottom cover extension sized for attachment to said downwardly extending bottom cover region, said bottom cover extension being sized to provide a larger device body footprint and an additional height to the downwardly extending bottom cover region so as to assure said over-center locking of the web and latching of said stopper external annular bead into said locking flange annular recess so as to secure locking of the stopper into the orifice.

* * * * *